(12) United States Patent
Prygoski et al.

(10) Patent No.: US 11,883,243 B2
(45) Date of Patent: Jan. 30, 2024

(54) ASSESSMENT OF TENSION BETWEEN BONE ANCHORS

(71) Applicant: OrthoPediatrics Corp., Warsaw, IN (US)

(72) Inventors: Matthew Prygoski, North Liberty, IN (US); Richard Detlefsen, Warsaw, IN (US); Evangelos Tozakoglou, Fort Wayne, IN (US); John V. Daniluck, Indianapolis, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 0 days.

(21) Appl. No.: 17/087,281

(22) Filed: Nov. 2, 2020

(65) Prior Publication Data

US 2021/0128264 A1    May 6, 2021

Related U.S. Application Data

(60) Provisional application No. 62/928,730, filed on Oct. 31, 2019.

(51) Int. Cl.
*A61B 17/70*    (2006.01)
*A61B 90/00*    (2016.01)
(Continued)

(52) U.S. Cl.
CPC .......... *A61B 90/06* (2016.02); *A61B 17/0401* (2013.01); *A61B 17/7053* (2013.01);
(Continued)

(58) Field of Classification Search
CPC ........ A61B 17/70–7046; A61B 2090/061–064
See application file for complete search history.

(56) References Cited

U.S. PATENT DOCUMENTS 2,737,075 A    3/1956  Poirier et al.
3,141,372 A    7/1964  Benk
(Continued)

FOREIGN PATENT DOCUMENTS

EP    2238944    3/2010
WO   0238058    9/2001
(Continued)

*Primary Examiner* — Eduardo C Robert
*Assistant Examiner* — Steven J Cotroneo
(74) *Attorney, Agent, or Firm* — Gerald W. Roberts; John V. Daniluck; Dentons Bingham Greenebaum LLP

(57) ABSTRACT

A system for interconnecting bones includes an implantable member configured to be mechanically coupled to a first bone, configured to be mechanically coupled to a second bone, configured to provide substantially no resistance to compression of the implantable member, configured to support a tensile load within a predetermined range of tensile loads extending from a first load to a second load, configured to have a predetermined elasticity within the range of tensile loads, configured to have a first characteristic at the first load, and configured to have a second characteristic at the second load. The system also includes a means for measuring the first characteristic and the second characteristic. And the system includes a means for calculating a tension between the first bone and the second bone based on the first characteristic and the second characteristic.

13 Claims, 19 Drawing Sheets

(51) Int. Cl.
  *A61B 17/04* (2006.01)
  *A61B 17/56* (2006.01)
(52) U.S. Cl.
  CPC ... *A61B 2017/564* (2013.01); *A61B 2090/064* (2016.02); *A61B 2562/0223* (2013.01)

(56) References Cited

U.S. PATENT DOCUMENTS

| | | | |
|---|---|---|---|
| 3,176,316 A | 4/1965 | Bodell | |
| 3,968,725 A | 7/1976 | Holzhauer | |
| 4,146,022 A | 3/1979 | Johnson et al. | |
| 4,170,921 A | 10/1979 | Repass | |
| 4,187,558 A | 2/1980 | Dahlen et al. | |
| 4,312,260 A | 1/1982 | Morieras | |
| 4,599,084 A | 7/1986 | Nashef | |
| 4,643,178 A | 2/1987 | Nastari et al. | |
| 4,731,084 A | 3/1988 | Dunn et al. | |
| 4,792,336 A | 12/1988 | Hlavacek et al. | |
| 4,883,486 A | 11/1989 | Kopadia | |
| 4,917,699 A | 4/1990 | Chervitz | |
| 4,917,700 A | 4/1990 | Aikens | |
| 4,946,377 A | 8/1990 | Kovach | |
| 5,004,474 A | 4/1991 | Fronk et al. | |
| 5,011,484 A | 4/1991 | Breard | |
| 5,180,393 A | 1/1993 | Commarmond | |
| 5,296,292 A | 3/1994 | Butters | |
| 5,456,722 A | 10/1995 | McLeod et al. | |
| 5,552,883 A | 9/1996 | Busch-Vishniac et al. | |
| 5,562,736 A | 10/1996 | Ray et al. | |
| 5,609,634 A | 3/1997 | Voydeville | |
| 5,797,910 A * | 8/1998 | Martin | A61B 17/7044 606/57 |
| 6,019,736 A | 2/2000 | Avellanet et al. | |
| 6,110,210 A | 8/2000 | Norton et al. | |
| 6,159,165 A | 12/2000 | Ferrera et al. | |
| 6,171,310 B1 | 1/2001 | Giordano | |
| 6,214,047 B1 | 4/2001 | Melvin | |
| 6,338,734 B1 | 1/2002 | Burke et al. | |
| 6,436,099 B1 | 8/2002 | Drewry et al. | |
| 6,475,220 B1 | 11/2002 | Whiteside | |
| 6,547,778 B1 | 4/2003 | Sklar et al. | |
| 6,616,669 B2 | 9/2003 | Ogilvie et al. | |
| 6,712,852 B1 | 3/2004 | Chung et al. | |
| 6,833,005 B1 | 12/2004 | Mantas | |
| 7,160,285 B2 | 1/2007 | Sklar et al. | |
| 7,326,249 B2 | 2/2008 | Lange | |
| 7,740,657 B2 | 6/2010 | Brown et al. | |
| 8,123,806 B1 | 2/2012 | Hoof | |
| 8,197,485 B2 | 6/2012 | Marshall et al. | |
| 8,206,446 B1 | 6/2012 | Montgomery | |
| 8,771,352 B2 | 7/2014 | Martin | |
| 8,790,357 B1 | 7/2014 | Hoof | |
| 8,870,955 B1 | 10/2014 | Montgomery | |
| 9,101,417 B2 | 8/2015 | Beyar et al. | |
| 9,101,427 B2 | 8/2015 | Globerman et al. | |
| 9,216,078 B2 | 12/2015 | Conner et al. | |
| 9,526,549 B2 | 12/2016 | Beyar et al. | |
| 10,617,458 B2 | 4/2020 | Beyar et al. | |
| 11,172,964 B1 * | 11/2021 | Chen | A61B 17/7032 |
| 2001/0049483 A1 | 5/2001 | Reay-Young | |
| 2001/0041938 A1 | 11/2001 | Hein | |
| 2002/0068975 A1 | 6/2002 | Teitelbaum et al. | |
| 2003/0092969 A1 * | 5/2003 | O'Malley | A61B 17/02 600/216 |
| 2003/0229396 A1 | 12/2003 | Andrews | |
| 2004/0062786 A1 * | 4/2004 | Ascenzi | A61B 17/58 703/11 |
| 2004/0230302 A1 | 11/2004 | May et al. | |
| 2005/0033301 A1 | 2/2005 | Lombardo et al. | |
| 2005/0090827 A1 | 4/2005 | Gedebou | |
| 2005/0192581 A1 | 9/2005 | Molz et al. | |
| 2007/0233151 A1 | 2/2007 | Chudik | |
| 2007/0191832 A1 | 8/2007 | Trieu | |
| 2007/0225763 A1 | 9/2007 | Zwolinski et al. | |
| 2007/0239158 A1 | 10/2007 | Trieu et al. | |
| 2008/0188936 A1 | 2/2008 | Ball et al. | |
| 2008/0108993 A1 | 5/2008 | Bennett et al. | |
| 2008/0140122 A1 * | 6/2008 | Bethell | A61B 17/7022 606/257 |
| 2008/0140202 A1 * | 6/2008 | Allard | A61B 17/7011 606/151 |
| 2008/0177168 A1 | 7/2008 | Callahan et al. | |
| 2010/0094355 A1 | 4/2010 | Trenhaile | |
| 2010/0094423 A1 | 4/2010 | Foley et al. | |
| 2010/0137908 A1 | 6/2010 | Zhang | |
| 2011/0313323 A1 * | 12/2011 | Henderson | A61B 17/7055 606/279 |
| 2013/0090521 A1 * | 4/2013 | Lau | A61L 17/06 606/230 |
| 2013/0096612 A1 | 4/2013 | Zajac et al. | |
| 2013/0096677 A1 | 4/2013 | Myers et al. | |
| 2013/0268073 A1 | 6/2013 | Albertorio et al. | |
| 2015/0094762 A1 | 4/2015 | Spenciner | |
| 2015/0157449 A1 | 6/2015 | Gustafson et al. | |
| 2015/0196385 A1 | 7/2015 | Kam et al. | |
| 2015/0272720 A1 | 10/2015 | Marks et al. | |
| 2017/0196508 A1 * | 7/2017 | Hunter | A61F 2/442 |
| 2019/0021768 A1 * | 1/2019 | Milbrandt | A61B 17/7005 |
| 2019/0380782 A1 * | 12/2019 | McAfee | A61F 2/4455 |
| 2021/0113213 A1 * | 4/2021 | Dahl | A61F 5/32 |
| 2022/0071670 A1 * | 3/2022 | Cheng | A61B 17/7016 |
| 2022/0160294 A1 * | 5/2022 | Metcalf | A61B 5/076 |
| 2022/0280199 A1 * | 9/2022 | Chen | A61B 17/7022 |

FOREIGN PATENT DOCUMENTS

| | | |
|---|---|---|
| WO | 2008002550 | 6/2007 |
| WO | 2008070452 | 11/2007 |
| WO | 2009129269 | 4/2009 |
| WO | 2011005966 | 7/2010 |
| WO | 2012154891 A3 | 11/2012 |
| WO | 2016164588 | 4/2016 |

* cited by examiner

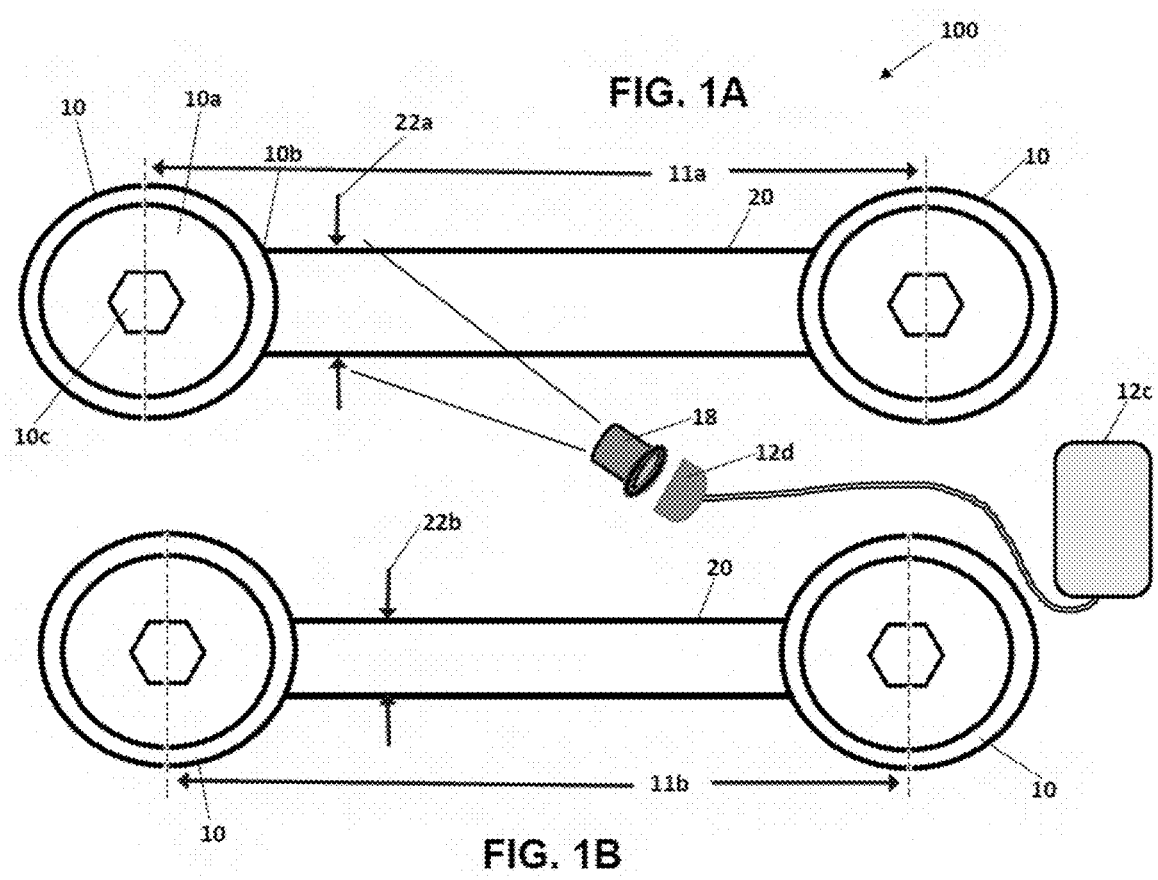

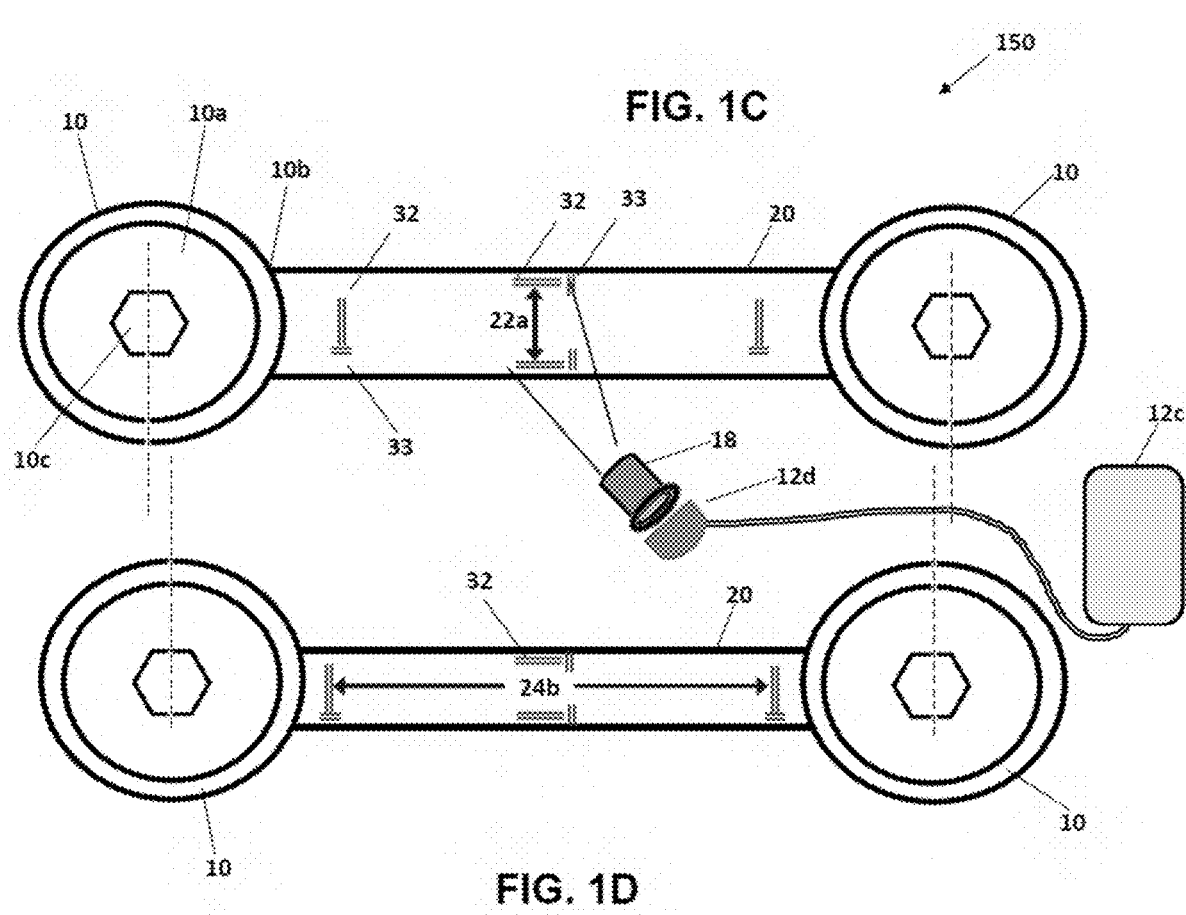

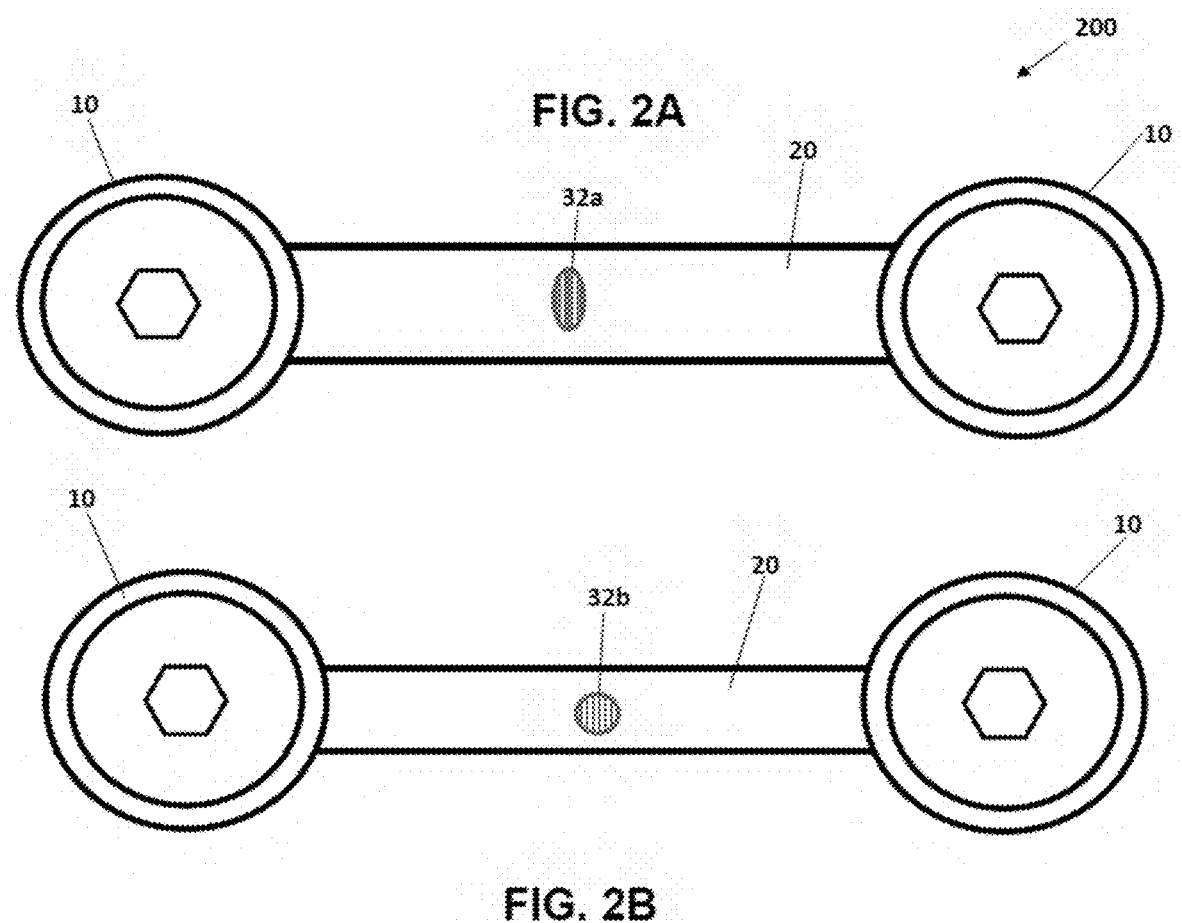

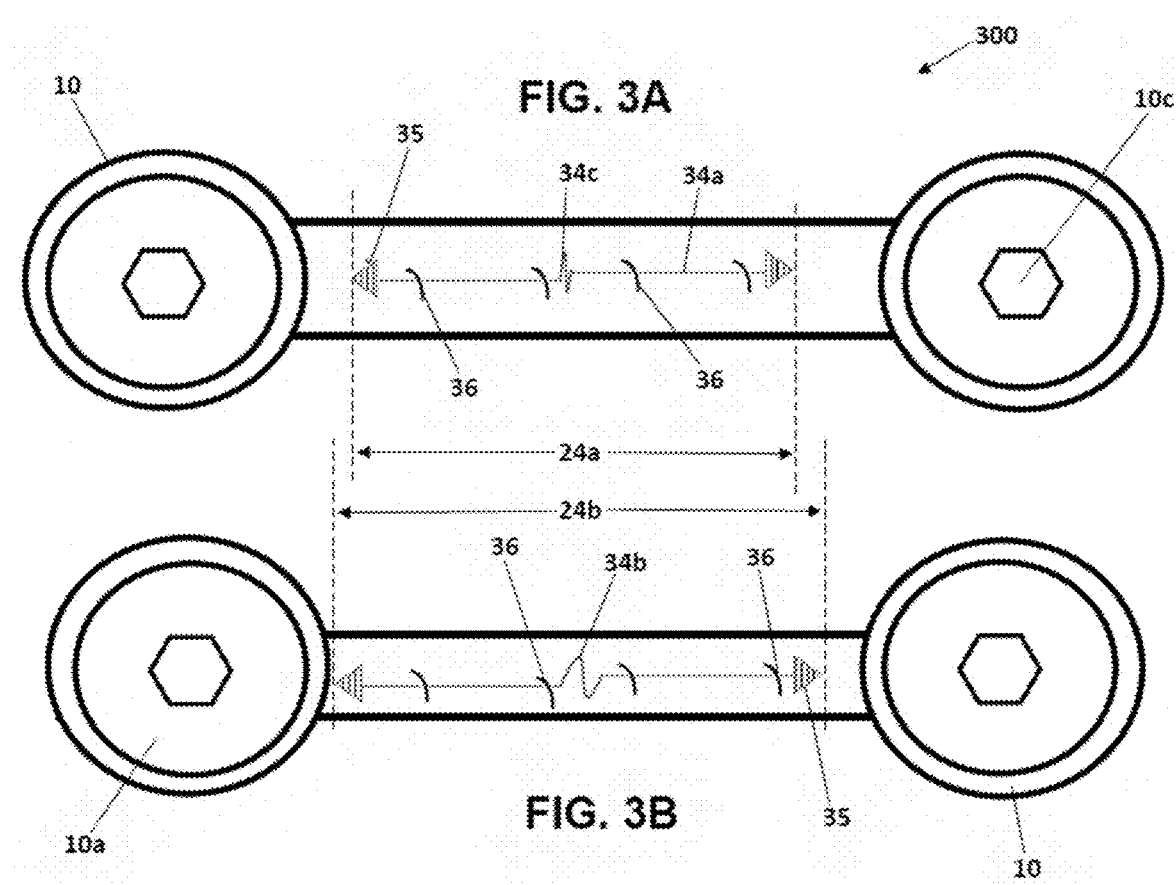

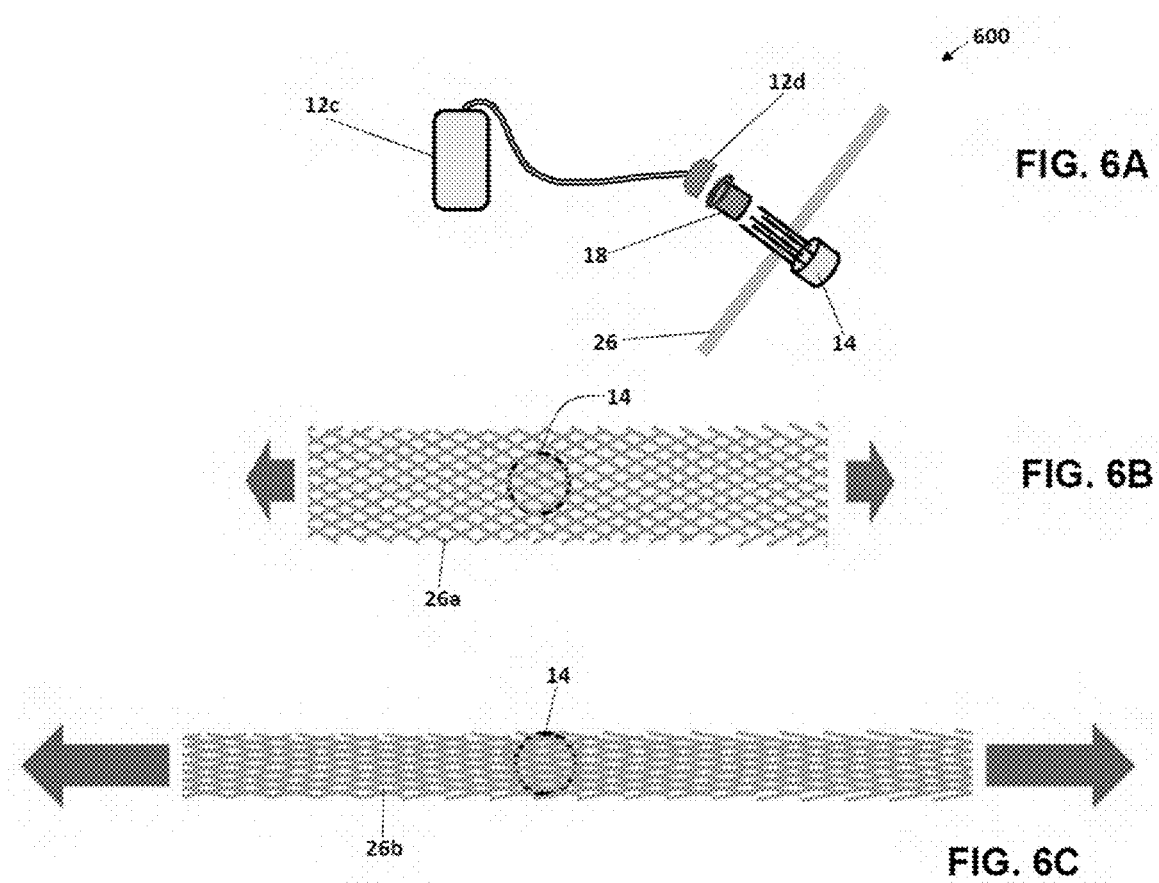

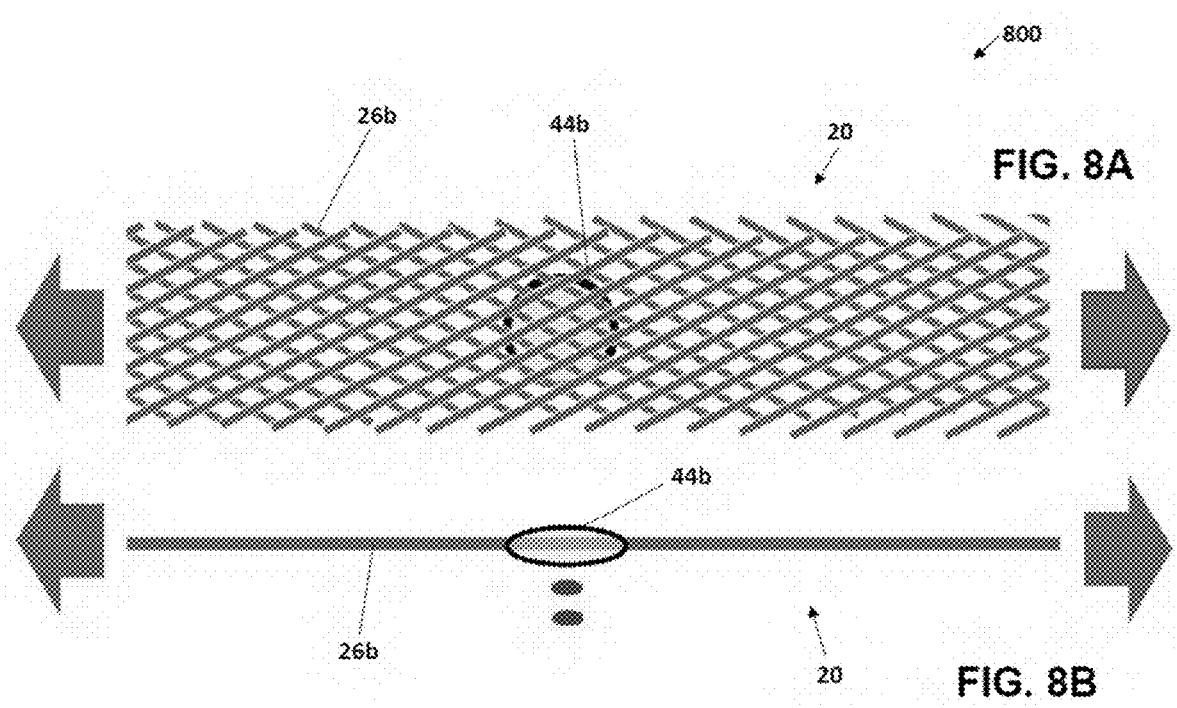

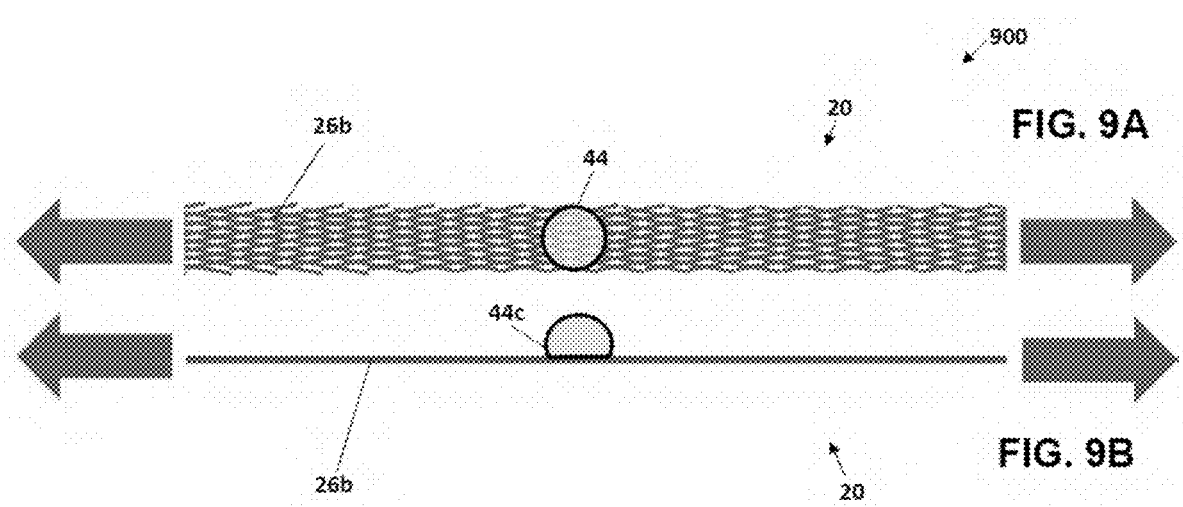

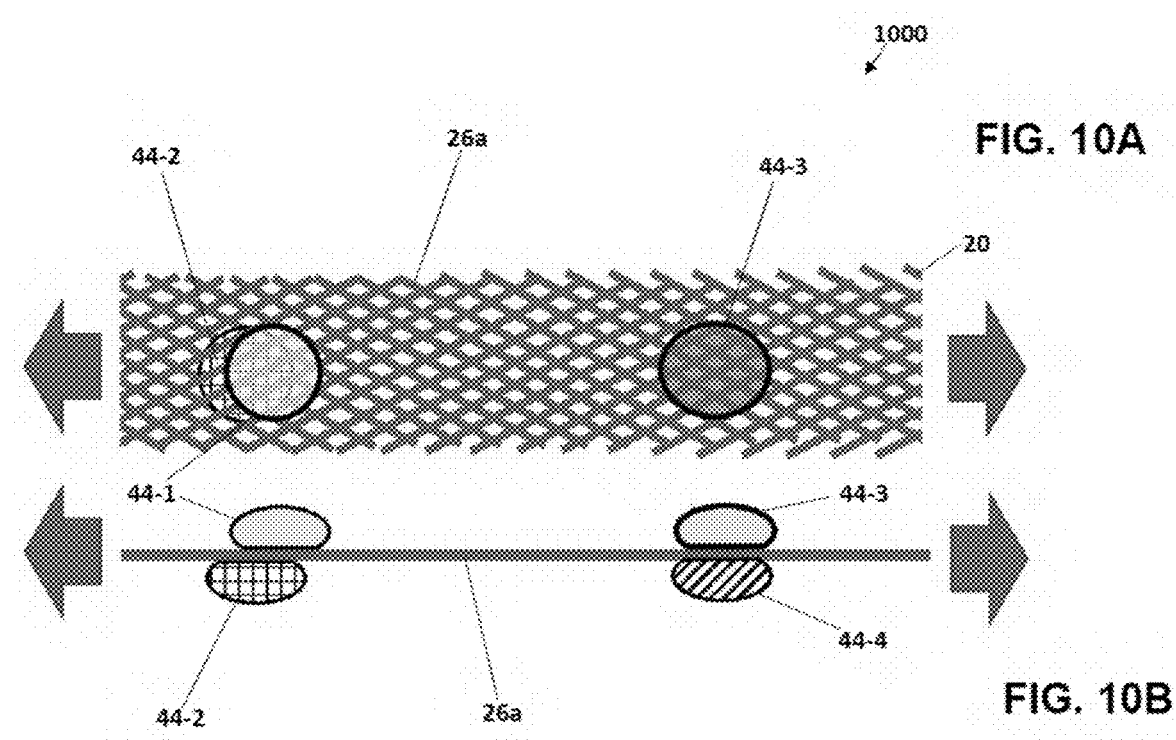

ASSESSMENT OF TENSION BETWEEN BONE ANCHORS

CROSS REFERENCE TO RELATED APPLICATIONS

This application claims the benefit of priority to U.S. Provisional Patent Application Ser. No. 62/928,730, filed Oct. 31, 2019, titled ASSESSMENT OF TENSION BETWEEN BONE ANCHORS, attorney docket 619067.100112, which is incorporated herein by reference.

FIELD OF THE INVENTION

Aspects of the present disclosure pertain to the field of orthopedics and, more particularly, to apparatuses and methods for coupling one or more bones or bone fragments to each other.

BACKGROUND

The Vertebral Body Tethering procedure modulates the growth of the spine by tensioning the convex side of the spine and allowing the concave side of the spine to continue growing. Achieving and maintaining the correct amount of tension between vertebrae is important to appropriately modifying such growth. Some implant and instrument concepts have been developed that can measure the tension in a section of tether during the tensioning portion of the procedure. However, historically, once such constructs have been tensioned and locked there have been few options left to assess the tension in the tethers.

There is a need to be able to continue to monitor the tension in a section of tether during the index procedure, for example, to see if tensioning a neighboring section affects the section of interest. There is also a need to continue monitoring the tension in a section over the course of the life of the implant to see if the level of tension goes higher or lower than desired.

SUMMARY OF THE INVENTION

Some embodiments provide a system for interconnecting bones. The system comprises an implantable member configured to be mechanically coupled to a first bone, configured to be mechanically coupled to a second bone, configured to provide substantially no resistance to compression of the implantable member, configured to support a tensile load within a predetermined range of tensile loads extending from a first load to a second load, configured to have a predetermined elasticity within the range of tensile loads, configured to have a first characteristic at the first load, and configured to have a second characteristic at the second load. The system also comprises a means for measuring the first characteristic and the second characteristic. And the system also comprising a means for calculating a tension between the first bone and the second bone based on the first characteristic and the second characteristic.

Some embodiments provide a method for applying a tension force between a pair of bone anchors. The method comprises the steps of attaching a first bone anchor to a first vertebra, attaching a second bone anchor to a second vertebra, attaching a first portion of a flexible member to the first bone anchor, and attaching a second portion of the flexible member to the second bone anchor such that there is slack in the middle portion of the flexible member between the first and second portions. The method also comprises reducing the length of the middle portion and removing the slack, measuring the size of a feature of the middle portion after removing the slack, tensioning the middle portion after said measuring, remeasuring the size of the feature of the middle portion after said tensioning, and comparing the measured size to the remeasured size and determining the state of tension in the middle portion.

BRIEF DESCRIPTION OF THE DRAWINGS

Some of the figures shown herein may include dimensions. Further, the figures shown herein may have been created from scaled drawings, scaled models, or from photographs that are scalable. It is understood that such dimensions, or the relative scaling within a figure, are by way of example, and not to be construed as limiting unless so stated in a claim. Persons of ordinary skill will also recognize that CAD renderings may include lines that pertain to changes in surface geometry, and not necessarily to component features.

FIG. 1A is a top plan view schematic representation of a pair of bone anchors interconnected by a flexible member according to one embodiment of the present invention, prior to tensioning.

FIG. 1B is a view of the apparatus of FIG. 1A after tension has been applied.

FIG. 1C is a top plan view schematic representation of a pair of bone anchors interconnected by a flexible member according to another embodiment of the present invention, prior to tensioning.

FIG. 1D is a view of the apparatus of FIG. 1A after tension has been applied.

FIG. 2A is a top plan view schematic representation of a pair of bone anchors interconnected by a flexible member according to another embodiment of the present invention, prior to tensioning.

FIG. 2B is a view of the apparatus of FIG. 2A after tension has been applied.

FIG. 3A is a top plan view schematic representation of a pair of bone anchors interconnected by a flexible member according to another embodiment of the present invention, prior to tensioning.

FIG. 3B is a view of the apparatus of FIG. 3A after tension has been applied.

FIG. 6A is a schematic representation of a system for measuring tension in a flexible connector.

FIG. 6B is a portion of the apparatus of FIG. 6A represented in a top plan view, prior to tensioning.

FIG. 6C is a portion of the apparatus of FIG. 6A represented in a top plan view, after tensioning.

FIG. 8A is a top plan view of a system for measuring tension in a flexible member according to another embodiment of the present invention, prior to tensioning.

FIG. 8B shows the apparatus of FIG. 8A, except after tensioning.

FIG. 9A is a top plan view schematic representation of a portion of a system for measuring tension in a flexible member, prior to tensioning.

FIG. 9B is a side elevational view of the apparatus of FIG. 9A.

FIG. 10A is a top plan view schematic representation of a system for measuring tension in a flexible member according to another embodiment of the present invention.

FIG. 10B is a side elevational view of the apparatus of FIG. 10A.

ELEMENT NUMBERING

Figure 4A:
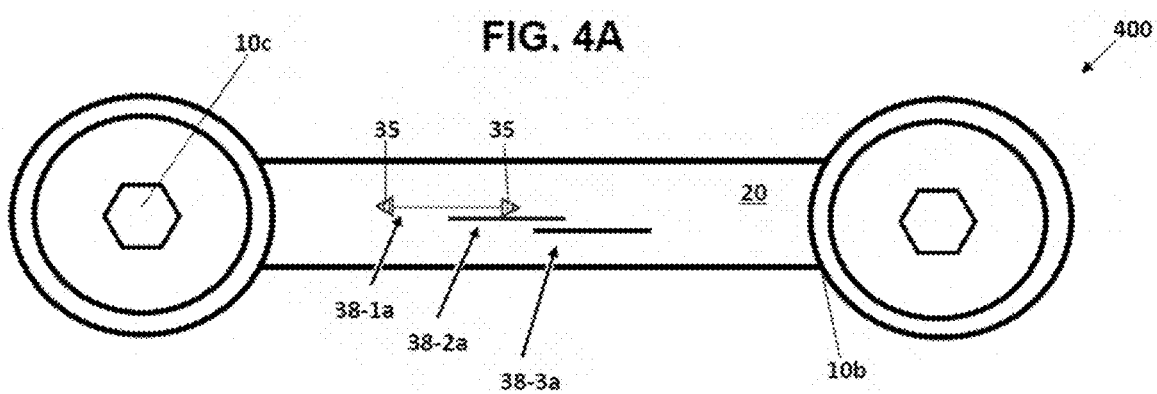
FIG. 4A is a top plan view schematic representation of a pair of bone anchors interconnected by a flexible member according to another embodiment of the present invention, prior to tensioning.

The following is a list of element numbers used with all of the embodiments, and at least one noun used to describe that element. The "X" for all of these numbers is removed or replaced with a number (0 or greater) in the text and drawings of this application. Consistent with statements made elsewhere in this specification, these various 2-digit element numbers are used among multiple embodiments, and aspects of a particular element stated for one embodiment can be applied to the same element number in a different embodiment, except as shown and described differently, and as would be understood by a person of ordinary skill in the art. It is understood that none of the embodiments disclosed herein are limited to these nouns, and these element numbers can further include other words that would be understood by a person of ordinary skill reading and reviewing this disclosure in its entirety.

| | |
|---|---|
| 10 | Tethering Bone anchoring assembly |
| A | Head |
| B | First Tether pathway |
| C | Locking screw |
| D | Bone screw |
| E | Staple |
| F | Second tether pathway |
| g | Bone screw |
| 11 | Distance between anchors |
| a | Pretensioning |
| B | Post tensioning |
| 12 | recording device |
| A | Optical |
| B | Radiographic |
| c | Smart phone |
| d | Sensor |
| 14 | Light source |
| 16 | Magnetic source |
| 18 | Portal |
| 20 | flexible member, flexible connector, tether, sutures, cables, springs, tape, and any of woven, braided, flat, organic or metallic as examples |
| A | First segment |
| B | Second segment |
| 21 | Second tether |
| 22a | Width pre tensioning |
| b | Width post tensioning |
| 24a | length pre tensioning |
| B | length post tensioning |
| 26 | Weave; braid; knitting |
| A | Pre tensioning |
| B | Post tensioning |
| 28 | Middle portion |
| 29 | Tether interconnection; suture; clamp |
| 32 | Printed symbol; visual marker |
| A | shape pre tensioning |
| B | shape post tensioning |
| 33 | Calibration marker |
| a | Longitudinal |
| B | Width |
| 34 | Embedded Deformable suture |
| A | shape pre tensioning |
| b | shape post tensioning |
| c | Middle portion |
| 35 | Anchor |
| 36 | Guide |
| 38 | In line Fuse; breakable suture |
| | shape pre tensioning |
| | shape post tensioning |
| 39 | Fold enclosing Fuse; breakable suture |
| | shape pre tensioning |
| | shape post tensioning |
| 40 | Radiopaque marker |
| a | First set |
| b | Second set |
| 44 | dye |
| a | Spot size, pre tensioning |
| b | Spot size, post tensioning |
| c | drop |
| d | color |
| 46 | Magnetic body |
| 50 | linear spring |
| A | length pre tensioning; |
| B | length post tensioning; |
| 52 | Preloaded spring |
| A | coils in contact |
| B | coils not in contact |

DETAILED DESCRIPTION OF ONE OR MORE EMBODIMENTS

Various aspects of the present disclosure provide apparatuses and methods for assessing or modulating tension in a flexible connection between bone anchors. Various aspects of the present disclosure provide apparatuses and methods for measuring the tension in a section of tether without having to directly grip onto it. Various aspects of the present disclosure provide for largely non-contacting (e.g., visual) tension assessment. Various aspects of the present disclosure provide integral features designed into the tether to facilitate tension assessment. Various aspects of the present disclosure provide other useful apparatuses, methods, features, and advantages.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It should be understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it should be understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that some features 1020.1 and 20.1 may be backward compatible, such that a feature of a later discussed embodiment (NXX.XX) may include features compatible with other various embodiments that were discussed earlier (MXX.XX) as would be understood by those of ordinary skill in the art. This description convention also applies to the use of prime ('), double prime ("), triple prime ('") and star or asterisk (*) suffixed element numbers. Therefore, it is not necessary to describe the features of 20.1, 20.1', 20.1", 20.1'" and 20*  that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

FIGS. 1A, 1B, 1C, and 1D depict two embodiments 100 and 150, respectively, of the present invention in which a visual measurement is made of the Poisson Effect of a flexible connector as that flexible connector is tensioned. Referring to FIG. 1A, it can be seen that a flexible connector or tether 20 interconnects two adjacent tethering bone anchoring assemblies 10. Each end of the tether is accepted within a corresponding tether pathway 10b of the head 10a of the corresponding tethering bone anchoring assembly. The tether extends internally through pathway 10b, and to a location where the tether can be locked in place by a locking assembly such as set screw 10c. When first installed, the tether 20 is loose between the two bone anchors, but can be tightened either by a separate tool (not shown) or by an adjustment mechanism built into anchoring assembly 10 (no shown), and once tightened can be locked into place so as to maintain a tension force between the two bone anchors. In the various embodiments shown herein, bone anchors such as those described with regards to bone anchor assembly 10 can be used with any of the various systems or methods shown herein. However, it is understood that other designs of bone anchoring assemblies can also be used.

FIG. 1B shows the assembly 100 of FIG. 1A after tension has been applied to tether 20. FIG. 1B shows that the anchor assemblies 10 are spaced apart by a distance 11b, which can be a smaller distance than the original, loose configuration of FIG. 1A (as represented by arrows 11a). Further, the untensioned tether 20 of FIG. 1A can be seen to leave a first, pre-tensioned width 22a, such as a diameter of a rounded tether, or the distance across a flat tether. Further, it is understood that with regards to a flat tether, the width measurement can also be made vertically or parallel to the attachment access of the bone anchors (for those embodiments in which the flat tether is so aligned.

FIG. 1B shows that after the tether 20 is tensioned, that the width 22b will decrease, as best understood by consideration of the Poisson Effect. In some embodiments, the width of the tether is measured radiographically (for those embodiments including radiopaque tethers), or visually. As shown with FIG. 1A, in some embodiments the width of the tether can be measured by a smart phone or other processor 12c that receives a signal corresponding to an image of the tether by a detector 12d that is able to view the tether through a portal 18.

In one method, the first, pre-tensioned distance measurement is made and interpreted by processor 12c, followed by a second distance measurement of the tensioned tether 20. The processor then calculates the difference between measurements 22a and 22b, and compares that distance to data (such as a look-up table), or uses that difference calculation in an equation and calculates an amount of tension that would be required to result in that change in tether width.

Methods 100 and 150 use the Poisson Effect to correlate axial tension in the tether to a reduction in width. Tethers are sometimes made of braided, woven, and/or sewn structures which tend to have a decrease in width as crossing fibers align under tension. In the present disclosure and the claims, the terms "braided," "woven," "sewn," "stitched," "knitted," "braid," "weave," "stitching," and "knitting" (and all inflections of these terms) are used interchangeably except where particular exclusion of one of more of such terms is expressly stated. The decrease in width could be detected with markers on the tether or by a vision system (for example, a camera-based smartphone app). A look-up table or calculation could convert the width measurement into an approximate tensile value based on correlations developed during bench testing. If the tether was created from a radiopaque material this analysis could be performed on x-ray and/or CT images which would non-invasively provide surgeons information about tension in the VBT construct.

FIGS. 1C and 1D depict a system 150 that utilizes a two dimensional Poisson Effect in the calculation of tether tension. FIG. 1C shows a tether 20 having a plurality of printed symbols or visual markers 32. FIG. 1C shows that tether 20 includes two pairs of symbols 32. The first pair is located proximate to each bone anchor 10. A second pair of markers 32 are located in a middle portion of tether 20. In some embodiments, each marker is a pair of closely spaced lines, dots, or other indicia.

FIG. 1C also shows a first set of tether measurements being made optically by way of a detector 12d looking through a portal 18 onto tether 20. The signal from detector 12d is provided to a processor 12c such as a smart phone. FIG. 1C shows that the processor receives data corresponding to the pre-tensioned width 22a between the middle pair of markers 32. Likewise, a pre-tensioned measurement 24a can be made between the pair of markers located proximate to corresponding bone anchors. A still further measurement of the distance between the closely spaced pair of indicia can also be made by processor 12c and this measurement can be made once for each of the four different markers. Although what has been shown and described as the use of a pair of closely spaced symbols, it is understood that yet other embodiments of the present invention contemplate the use of either single symbols, or pluralities of symbols. In some embodiments, the closely spaced grouping of multiple symbols allows for improved detection of the grouping by the processing software.

FIG. 1D shows the configuration of the tether and bone anchors after tension has been applied and locked into the bone anchors. As also seen in FIGS. 1A and 1B, the application of tension to tether 20 can cause a decrease in the distance between the bone anchors (although such a change in bone anchor position is not required for the apparatus or methods discussed herein).

Referring again to FIG. 1D, it can be seen that the lengthwise distance measurements between the lengthwise-oriented markers 32 corresponds to the longer, stretched distance 24b between the pair of markers. Still further, the distance between the central pair of markers 22b will be less than the untensioned distance 22a shown in FIG. 1C. Therefore, in making two dimensional measurements, the degree of tension in tether 20 will result in an increase of the length of the tether, and at the same time, a decrease in the width of the tether. In this method 150 a more accurate measurement of tension can be obtained by comparing the pre-tensioned and post-tensioned ratio of the width to the length. Therefore, even if the change in the length and width dimensions are small, by forming the ratio of the changes (i.e., one of the numerator or denominator increasing and the other one decreasing) a more robust, accurate prediction of tension courses will be obtained.

Still further, it is possible to correct the distance measurements by use of calibration markers 33. Each calibration marker, similar to the main markers 32, preferably includes a pair of closely-spaced symbols, or a symbol having well-defined and observable boundaries. In some embodiments, processor 12c through detector 12d can measure the distance between the pair of closely-spaced symbols 32, or the pair of closely-spaced symbols 33. Since the distance between closely-spaced symbols 32 are subjected to only marginal Poisson Effect (because the distance between adjacent markers is much less than the width 22 of the tether), the measured distance between a pair of symbols 32 can be expected to undergo only marginal Poisson Effect during tensioning.

In still further embodiments, the calibration markers can be used to further remove unwanted Poisson Effects during calibration. In one embodiment it can be seen that each calibration marker is a pair of lines oriented and spaced apart such that any localized Poisson Effect will be even further diminished than the effect on a symbol 32. For example, considering the marker 33 at the top center of tether 20 in FIG. 1C, it can be seen that the spacing between the two vertical parallel lines may not be affected at all by the Poisson thinning effect that occurs at the width. Although the length of that marker 33 may be affected a centralized thinning of tether 20, the space between the two vertical, parallel lines will be changed only by the lateral stretching. Since the original distance between the two lines is small, the Poisson stretching Effect will be even smaller.

FIGS. 2A and 2B show apparatus and methods 200 for visually assessing tension accordingly to another embodiment of the present invention. A flexible connector or tether 20 is shown interconnecting to bone anchors 10. Tether 20 includes a printed symbol or visual marker 32 located preferably on the surface of the tether, although it is understood that the printed material or symbol could also be located within the interior of a woven tether. In various alternative embodiments, the visual marker 32 may comprise laser-markings, colored dyes, differently colored woven strands, or any other suitable markings. In one embodiment, the symbol is located in the middle portion of the tether between the adjacent bone anchors.

Prior to tensioning, and when the tether is supporting relative little tension, other than the tension due to its weight, and also including situations in which the middle portion of the tether includes slack, the printed material 32a has a shape. In some embodiments, the processor includes software that is adapted and configured to look for the unstretched, originally printed shape. If the user indicates to the software that the pre-tensioned shape should be appearing in the detected image, and if that detected image is not sufficiently similar to an image of the unstretched marker stored in memory, the processor can send a software notification to the user that there is an error in this initially detected image. This error could be due to flexing of the tether, slack in the tether, unwanted obstruction of the image of the tether, or other reasons. By providing this error message, the surgeon can make the appropriate corrections in the preload, remove any blockage in the line of sight of the image, or take other actions.

After tension is applied, the shape of marker 32 changes as a result of the tension. As shown in FIG. 2B, the length of the tether has expanded, which changes the lateral dimension of the marker. Likewise, in those tethers that undergo a Poisson Effect, the width of the tether has decreased, which likewise changes the corresponding width of the marker. As one example, the marker 32 has a two dimensional shape that changes from having one axis of symmetry (as shown in FIG. 2A) to having two axes of symmetry (as shown in FIG. 2B). The initial, pre-tension shape 32a is adapted and configured to achieve a generally symmetrical shape 32b at a pre-determined amount of tension in tether 20.

Similar to the apparatus and method discussed relative to FIGS. 1C and 1D, the symbol shown in FIGS. 2A and 2B likewise provides two dimensional, visual information to the processor and to the surgeon. In still further embodiments, the apparatus and method 200 of FIGS. 2A and 2B further includes the use of a processor 12c receiving an electrical signal corresponding to a visual shape from a detector 12d, especially if viewed through a portal 18. It is further understood that any of the apparatus and methods described herein can benefit from the use of optical detection systems, or likewise, with tethers including radiopaque markers, provide useful information by way of x-ray).

This method 200 correlates axial stretch in the tether to axial tension. A marker is placed on the tether and as the tether stretches the marker becomes distorted. In the example of FIG. 2A, the oval-shaped image on the tether stretches into a circle at a given tension value. Different marks could be placed on the tether that stretch into the desired shape at different tension levels. For example, one image may become a perfect circle at 50 N, another at 100 N, and another at 200 N.

The tether could be marked in a pre-stretched state during manufacture. To follow the example above, the tether could be stretched to 50 N and marked with a circle, then stretched to 100 N and marked with a circle, etc. If the mark was created from a radiopaque ink or woven into the tether with a radiopaque fiber this analysis could be performed on x-ray and/or CT images which would non-invasively provide surgeons information about tension in the VBT construct.

FIGS. 3A and 3B show pre-tensioned and post-tensioned views, respectfully, of apparatus methods 300 according to another embodiment of the present invention. Tether 20 includes an attached or embedded deformable apparatus 34, such as a suture. Preferably, the suture extends in one continuous length from the left side attachment location 35 to a right side attachment location 35, these locations being end points of suture 34, and also being locations where the suture is attached to tether 20. The suture 34 extends from one attachment point 35 to the other, preferably through one or more suture guides 36. These guides preferably keep the suture 34 from moving relative to the width of the suture, but do not inhibit the lengthwise movement of the suture as the tether stretches.

Located generally in the middle 34c of structure 34, is a pre-determined shape of the middle of the suture. In some embodiments, this middle portion is retained in this initial shape, either by use of elastic and resilient materials (i.e., spring-like), or as a matter of a frangible material that can break as the tether is tensioned. Preferably, this initial configuration can be considered compressed, yet including details that expand out into a recognizable shape. As shown in FIG. 3B, when the proper amount of tension is applied, deformable structure 34 expands into a sine wave representation. By using visual assessments (either by the naked eye, a processor and a detector, or x-rays, or the like) the tensioned shape shown in FIG. 3B can be correlated to a degree of tension in tether 20.

As compared to the discussion relative to FIGS. 2B and 1D, the structure show in FIG. 3B responds to uniaxial deflection, i.e., to the change in tether length from length 24a (pre-tensioned) to length 24b (post-tensioned). However, the central image in the middle portion of 34c, the central structure can have a two-dimensional shape to it. For example, the sine wave shown in FIG. 3A has a first, larger amplitude and a first, shorter wave length. In FIG. 3B, this central deformable structure has a second, smaller peak-to-peak amplitude, and a second, longer wave length. Therefore, even though the structure is responding to lengthwise (1-D) stretching of tether 20, the structure itself experiences a two dimensional change, which in some embodiments is more easily recognizable and detectable than a one dimensional change in the structure.

Alternatively, the mark on the tether could be created from a custom stitch pattern that deforms in a visually recognizable manner. An example of such stitch is shown in FIGS. 3A and 3B. In this example the angles of the stitch change as the tether stretches, causing an easily identifiable change in pattern. The change in shape could be correlated (via bench tests) to the amount of tension in the tether. A graphical based shape-tension chart could be provided to the user.

If the stitch was woven into the tether with a radiopaque fiber this analysis could be performed on x-ray and/or CT images which would non-invasively provide surgeons information about tension in the VBT construct. The stitch pattern could also be made from multiple segments. For example, two lines (parallel to one another, perpendicular to the axis of the tether) could be stitched into the tether. The user could measure the distance between the lines and correlate that to axial stretch of the tether, which in turn could be correlated to applied tension. Since changes in distance for a uniaxial central deformable structure are expected to be small, a vision system (e.g., smartphone-based camera app) could be useful.

Figure 4B:
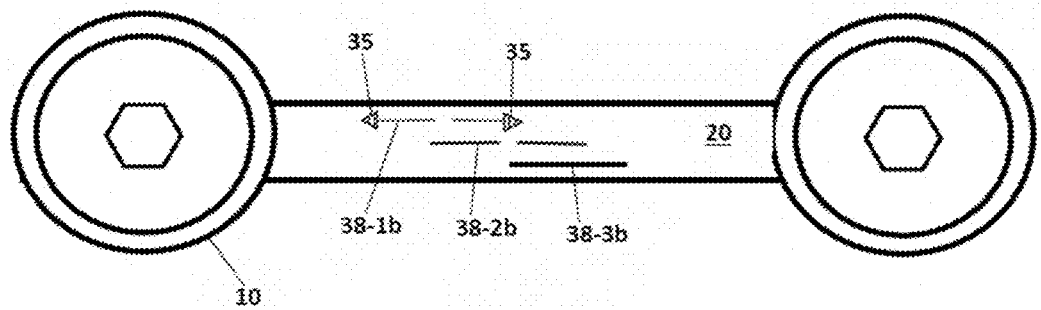
FIG. 4B is a view of the apparatus of FIG. 4A after tension has been applied.

FIGS. 4A and 4B show pre-tensioned and post-tensioned examples, respectively, of apparatus and methods 400 according to another embodiment of the present invention. Tether 20 includes in it at least one breakable structure 38 which is adapted and configured to break in correspondence with predetermined amounts of tension in tether 20. As shown in FIG. 4A, tether 20 includes three such in-line fuses 38, shown in their initial configurations 38-1a, 38-2a, and 38-3a. Each of these structures are adapted and configured to break when certain pre-determined forces are carried within that structure, with the dash 1 structure breaking at the lowest tension force, the dash 2 structure breaking at a higher tension force, and the dash 3 structure breaking at a higher tension force. It is understood that the tension force applied to a fuse 38 is a portion of the larger tensile load experienced by the complete tether 20.

FIG. 4B shows the three breakable sutures after tension has been applied to tether 20. Structures 38-1b and 38-2b are shown broken, and the break of these structures is preferably visually observable. However, structure 38-3b remains intact. Therefore, the tension in tether 20 correlates to a level of tension higher than that required to break structure 38-2, but lower than that required to break structure 38-3.

Tension is indicated by the fracture of one or more indicator fibers braided/woven/sewn into the tether along its length. Each indicator fiber's size/diameter/strength is chosen so that it breaks when a given load is applied to the tether. In the example below, there are 3 indicator fibers sewn into the tether. If the surgeon observes, for example, that the 5 lbf fiber is broken but the 10 lbf fiber is not, it can be concluded that the axial tension in the tether is somewhere between 5-10 lbf.

This method of tension assessment could be utilized during the index surgery as a section of tether is tensioned with a tensioning instrument. It could also be used during the index surgery to ensure that too much additional tension is not being to an already tensioned level as a neighboring section of the tether is being tensioned. Alternatively, if the indicator fibers were constructed of a radiopaque filament, the surgeon could assess post-operative tension changes non-invasively via x-ray or CT. In addition to indicating "normal" amounts of tension, an indicator fiber could also be designed to break at a relatively high force, warning of pending tether failure.

Fracture of the indicator fibers occurs when there is axial stretch of the tether. It is understood that various embodiments of the present invention contemplate any type of "fuse" or structure, and any method of incorporating such fuses into the tether. As examples, fracture of the indicator fibers could be ensured in at least two ways:

1) The indicator fibers are woven/sewn/braided into the tether as an integral part of the weave/braid. The material of the indicator fibers is chosen so that it is more brittle than the remaining fibers in the braid. This difference in elasticity allows the indicator fibers to fracture before the rest of the tether. A correlation could be developed between axial tether tension, stretch of the tether and indicator fibers, and fracture strength of the fibers. The correlation is helpful because in this configuration there is load sharing between the tether and indicator fiber(s) because the indicator fiber(s) are an integral part of the tether construction.
2) The distal ends of the indicator fiber could be anchored into tether when the tether is in a relaxed state as shown for fuse 38-*a*. The remaining section of indicator fiber would be free to slide relative to the tether. In this way, any applied tension that stretches the tether is directly applied to the ends of the indicator fiber. This method makes for a simple 1:1 correlation between tether tension and indicator fiber tension.

Figure 5:
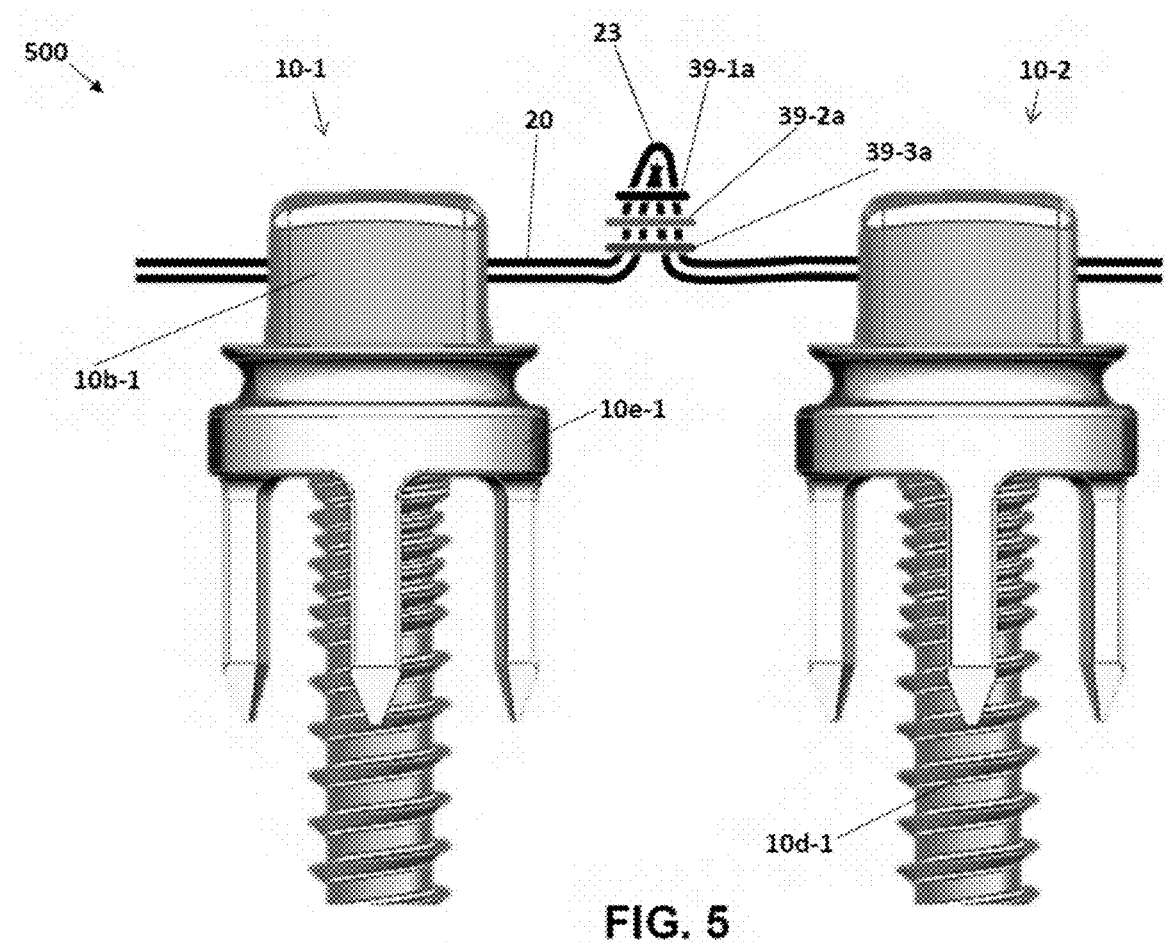
FIG. 5 is a side elevational schematic representation of a pair of bone anchors interconnected by a flexible member, prior to tensioning.

FIG. 5 is a side elevational schematic representation of apparatus and methods 500 for modulating tension according to another embodiment of the present invention. A tether 20 is shown with opposing ends located in different tether pathways 10*b* of adjacent bone anchors 10. In one embodiment, tether 20 includes a folded section 23, in which a portion of tether is bundled to itself by one or more breakable sutures 39. As shown in FIG. 5, a first breakable suture 39-3 is located furthest away from the fold, a second breakable structure 39-2 is located closer to the fold, and a third breakable structure 39-1 is located closest to the fold.

In one embodiment, suture 39-3 is selected to be strong enough such that the pre-tensioned fold configuration at the time of implantation is the same as the post-tension fold configuration at the time of implantation. However, as the bones to which the bond anchors are attached attempt to pull apart, a force within fuse 39-3 will be achieved at which point the fuse break, releasing additional looseness or slack into the tether 20, and thereby reducing the tensile force at the time of breakage. It is understood that the forces required to break any one of the sutures 39 can be of any magnitude in any order, various embodiments not requiring that these sutures be in order of increasing or decreasing break force.

Embodiment 500 preferably uses one or more sacrificial indicator fibers are used to signify when tension in a length of tether has exceeded a given value. However, rather than have the indicator fibers in line with the axis of the tether, the indicator fibers are used to stitch a fold of tether together as shown in the diagram below.

If tension in the tether increases above the strength threshold of an indicator fiber the indicator fiber will fracture. The surgeon can examine which fibers are broken to determine how much tension was generated in the tether.

One function of this concept is that fracture of an indicator fiber creates slack in the tether, resetting the tension load back to a lower value. After the tension is reset, it would take additional patient growth to generate enough tension in the tether to fracture a subsequent indicator fiber. In this way, a time history of the patient's growth/tensile loading can be generated (if the fracture of a radiopaque indicator fiber can be identified on x-ray or CT).

Since the tension is reset there is value to having several indicator fibers with the same fracture setting. Or the indicator fibers could be made to have different fracture strengths.

FIGS. 6A, 6B and 6C present various schematic representations of methods and apparatus 600 according to another embodiment of the present invention. FIG. 6A shows a system including a preferably woven flexible connector 26 that is located between a source of the electromagnetic radiation 14 and a corresponding detector 12*d*. In some embodiments, the flexible connector can also be a flat braid, which by way of filament tightening can exhibit more of a Poisson Effect.

As discussed previously, a signal from detector 12*d* is provided to a processor 12*c*, which can include a smart phone. Radiation emitted by source 14 passes through the weave 26 of the tether, through portal 18, and into detector 12. In some embodiments, the source 14 is a source of visible light, although it is understood that the emitter 14 and detector 12*d* can operate in any biologically compatible radiation band.

FIG. 6B shows a view of detector 14 as could be seen through portal 18. It can be seen that pre-tensioned weave 26*a* includes a first amount of porosity or transmissibility that permits the passage therethrough of a first amounts of radiation, which falls incident upon detector 12*d*. Referring to FIG. 6C, it can be seen that the post-tensioned weave 26*b* has a second, lesser amount of porosity or transmissibility, and for this reason, a smaller amount of radiation from emitter 14 passes through the weave onto detector 12*d*. The processor 12*c* calculates a difference in the transmitted radiation between pre-tensioned and post-tensioned tethers, and compares that difference to data previously acquired that shows the correspondence between porosity or transmissibility and tether tension.

Many tethers are constructed of braids of various materials. Numerous crossing yarns in the braid create porosity in the structure. As braids are tensioned, the crossing yarns tend to align with the applied loads and become closer with neighboring yarns, reducing the porosity in the structure.

Embodiment 600 includes assessing tension of a tether with a light source (e.g., low power laser) and optical sensor built into a surgical instrument in the following manner:

1) The instrument is placed around the tether so that the light source is on one side and the optical sensor is on the other. The laser is shined through the tether.
2) The optical sensor takes a reading of how much light (e.g., light intensity) is making its way through the tether (i.e., takes a reading of the opacity of the tether).
   a. A loose braid under low tension allows more light through (i.e., a loose braid under low tension is less opaque).
   b. A braid under high tension allows less light through (i.e., a braid under high tension is more opaque).
3) The ratio of input/transmitted light is then correlated to the amount of applied tension.

This method of assessing tension is described using a braid because it is simple to visualize the deformation of the yarns. However, it is possible this method could work with other tether constructions such as weaves or knits. Note that this method of tension measurement is non-contacting with the tether. It requires no unique features (markers, indicator threads, etc.) in the tether itself.

Figures 7A, 7B:
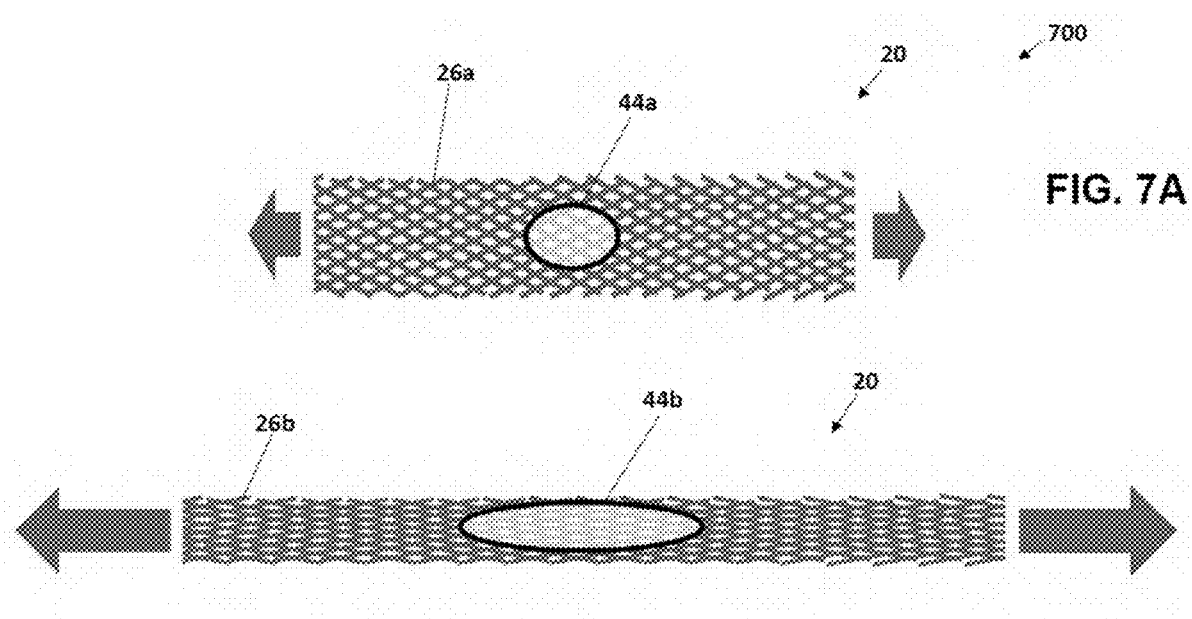
FIG. 7A is a top plan view of a system for measuring tension in a flexible member according to another embodiment of the present invention, prior to tensioning.
FIG. 7B shows the apparatus of FIG. 7A, except after tensioning.

FIGS. 7A and 7B show schematic representations of an apparatus and method 700 according to another embodiment of the present invention. System 700 includes a quantity of liquid dye 44 that is placed in contact with a braided or woven flexible connector. The dye 44 is selected based on properties that include the ability of the dye to wick along the surface of the tether. FIG. 7A shows a pre-tensioned drop 44a that has wicked by a first amount along the surface of a pre-tensioned woven tether 26a. FIG. 7B shows the size and/or shape of drop 44b to be different on the post-tensioned weave 26b. The size and/or shape of the drop can be correlated with the amount of tension in the flexible connector 20. Consistent with the other embodiments shown herein, system 700 can also employ a detector and processor (not shown) to aid in the analysis of the wick.

A tether (such as a braid) becomes more aligned and compact when tension is applied. This is true for the yarns that can typically be visualized and for the microfibers that make up each yarn. System 700 includes ways in which the tension-induced structural change in the braid can be detected/measured using liquid dye penetration. The liquid dye would be biocompatible to be used in vivo. These concepts can include tether constructed from a flat braid, but could be applied to round braids, weaves, etc.

A drop of dye could be placed on a section of tether and the surgeon could measure how far along the length of the tether the liquid wicks into the tether or along the surface of the tether in a given amount of time. A higher tension in the tether leads to more contact between fibers and yarns, which leads to a higher rate of wicking. The surgeon could correlate a dimensional change in the drop of dye to the tension in the tether. In FIGS. 7A and 7B, the dot represents a drop of dye that has been allowed to wick into the tether.

FIGS. 8A and 8B schematically depict apparatus methods 800 according to another embodiment of the present invention. FIG. 8A shows a drop that has penetrated into a tensioned weave 26b of tether 20. FIG. 8B is a side view of FIG. 8A. These figures show the drop 44b of dye after it has penetrated the weave or braid. The time required for the drop to transition from a pre-tensioned state (i.e., the initial contact of the drop with the tether 20, not shown) to the time at which the drop achieves a final degree of penetration can be measured and correlated to the tension in weave 26b. It is further understood that the various detectors and processors described herein can be used to make a video of the process of penetration, with the processor comparing the time response to a database for tether 20 of predetermined tension.

In some embodiments, the processor uses the data from the detected image to calculate the penetrated area as a function of time. Various different aspects of the detected image can be used for correlation against a database. As one example, the database can compare the tension in the tether (or the difference between pre-tensioned and post-tensioned values) to the initial and final spot areas, and not necessarily taking into account the time required for the size change. In yet other embodiments, the processor can calculate from the image (and also use in the database) the time-based rate of change of the area, such as a rate of change in terms of percent growth. In yet other embodiments, the processing software assesses the geometry of the final spot size (such as the ratio of maximum width to maximum length), and correlates this to a corresponding database of tension.

FIGS. 9A and 9B schematically represents apparatus and methods 900 according to yet another embodiment of the present invention. Apparatus and methods 900 differ from apparatus and methods 800 by observation of the initial and final states of the configuration of a substantially non-penetrating droplet 44, and in some embodiments without reference to time.

In some embodiments, the dyes 44 are selected based upon their surface tension or viscosity. In one embodiment, the drop 44 generally sits on the surface of the weave 26b that is post-tensioned. Should the drop 44c penetrate into the weave itself, then the dispersion of the liquid into the weave would indicate that a pre-determined amount of tension has been exceeded. A drop of dye could be placed on the surface of a tensioned tether. In some embodiments, the time for the drop of dye to penetrate the braid could be measured and correlated to tension. This would work because a tensioned braid is tighter and presents smaller pores for the liquid to penetrate. In yet other embodiments, at a given tension, the surface tension created by the tight microstructure of the braid may be sufficient enough to allow the bead of dye to sit on the surface of the braid. If the dye penetrates the braid, the surgeon knows the braid is under a given tension threshold. If the dye beads on the surface, the surgeon knows the braid is above a given threshold. Alternatively, dyes of different viscosity could be used to identify different thresholds of surface tension (and therefore microstructure and ultimately tension).

Figures 11A, 11B:
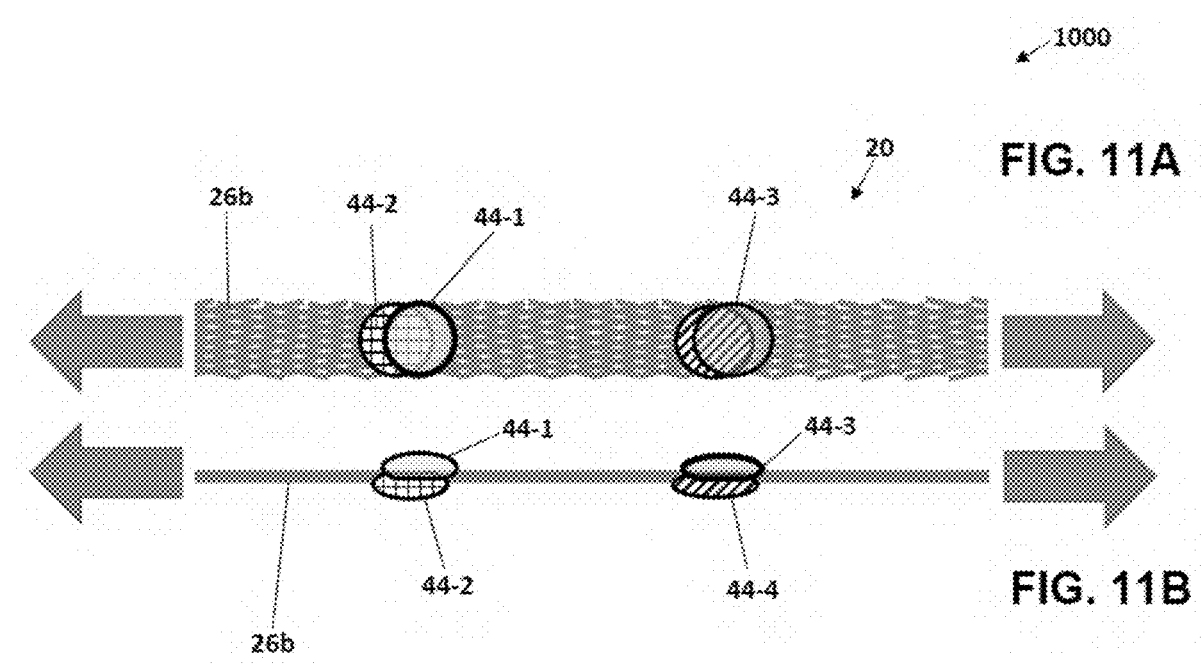
FIG. 11A is a view of the apparatus of FIG. 10A after the application of tension.
FIG. 11B is a view of the apparatus of FIG. 10B after the application of tension.

FIGS. 10A, 10B, 11A and 11B schematically depict apparatus and methods 1000 according to another embodiment of the present invention. FIGS. 10A and 10B show a woven, braided, or knitted tether 26a in its pre-tensioned state, and FIGS. 11A and 11B show the same tether in its post-tensioned state 26b. Referring to FIG. 10B, it can be seen that the pre-tensioned weave 26a can include one or more drops of dye 44-1 and 44-3 on one side of the tether 20. A second set of drops 44-2 and 44-4 are shown located on the opposite side of the tether, and generally opposite to one of the drops 44-1 or 44-3. The dyes 44 are selected to provide relatively little mixing, wicking, or penetration in the pre-tensioned state.

It is also understood that although FIGS. 10A and 10B show two pairs of opposite located quantities of dye 44, the present invention also contemplates those embodiments in which there is a single pair of oppositely placed drops 44, and also those embodiments in which there is a single pair of drops on the same side of tether 20. As one example, a single pair of drops on the same side of the tether can be from two different types of dyes, with one drop having surface tension, viscosity, color, or some other physical property that is different than the other drop. The two separated drops can react differently to tension, with one drop wicking, penetrating, or other demonstrating a different change at a lower amount of tether tension, and the other drop wicking, penetrating, or demonstrating another change at a higher level of tension. In yet another embodiment, the two drops on the same side of the tether are placed sufficiently close to one another that when a pre-determined amount of tension is achieved in the tether, that each drop wicks a first, limited amount into the tether. At a second, higher level of tension, the two expanded drop sizes wick even further and contact one another. At that point of contact, it is possible to detect a mixing of two different colors, such as a blue drop and a yellow drop mixing at this interface to form a green portion.

FIGS. 11A and 11B depict the tether 20 in its post-tensioned woven state 26b. In some embodiments, only a single pair of oppositely placed dye drops (such as 44-1 and 44-2), have achieved mixing at a first, pre-determined level of tension. In such embodiments, the second pair of dye drops (44-3 and 44-4) achieve a preferably distinguishable degree of mixing, penetration, or wicking at a second, higher pre-determined level of tension. By observation of which pairs of drops have mixed (such as by color recognition) or some other chemical or physical change in the mixed droplet the amount of tension can be determined, in a manner similar to that of other embodiments discussed herein wherein the color change or other change is detected electronically by a detector and assessed electronically by a processor, or in some embodiments in which the determination of tension is assessed by an observer of the droplets.

A drop of different colored dyes could be placed above and below the tether. The resulting color change (in a given amount of time) could indicate the amount of dye mixing that has occurred. Dye mixing could be correlated to porosity of the tether, which could in turn be correlated to tension in the tether. An absence of mixing would indicate that the surface tension created by the tight microstructure is high enough to keep the dyes beaded up on either surface of the tether. Differences in color may be slight and hard to perceive by eye so a vision system (e.g., smartphone camera app) may be helpful to analyze the color.

Figure 12:
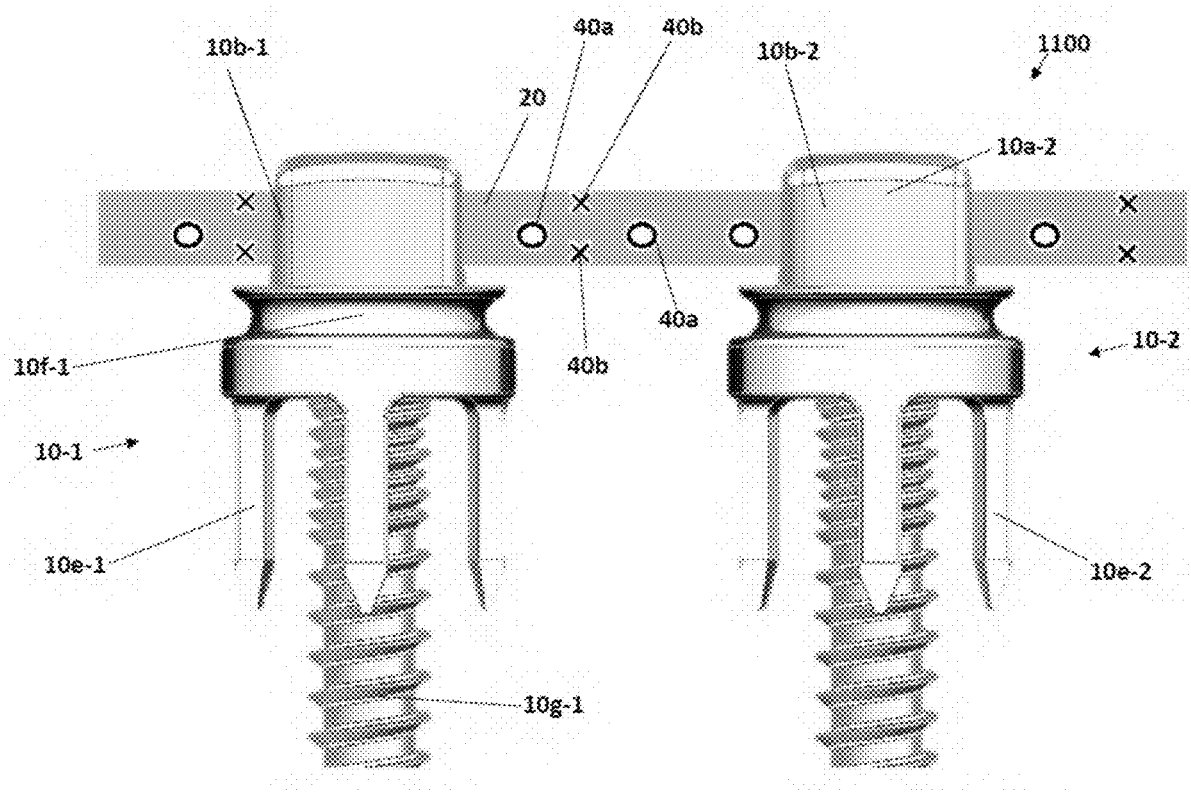
FIG. 12 is a side elevational schematic representation of a pair of bone anchors interconnected by a flexible member according to another embodiment.

FIG. 12 shows an apparatus and method 1100 according to yet another embodiment of the present invention. FIG. 12 shows a pair of adjacent bone anchoring assemblies 10-1 and 10-2. A tether 20 passes through each of the tether pathways 10b-1 and 10b-2. These tether pathways 10b pass within corresponding anchoring heads 10a being affixed to vertebrae by a corresponding bone screw 10g, and further located on the vertebrae by a staple 10e.

In a manner similar to that discussed relative to apparatus and methods 150, apparatus and methods 1100 includes a plurality of radiopaque markers 40 that are arranged so as to provide two dimensional information corresponding to the tension in tether 20. A pair of laterally aligned markers 40a are arranged along the length of tether 20. Further, in some embodiments, pairs of vertically arranged (i.e., width-arranged) markers 40b are arranged at locations along the length of tether 20. In a pre-tensioned state, the ratio of the distances between radiopaque markers 40a and between radiopaque markers 40b establish a baseline degree of tension. As the desired tension is achieved in tether 20, the spacing between laterally-arranged markers 40a increases, whereas the distance between vertically-arranged markers 40b decreases. Preferably, the ratios of pre-tensioned and post-tensioned measurements are determined by a processor that compares the pre and post ratios of vertical/horizontal spacings to a pre-existing database that relates such ratios to the state of tension.

In this embodiment 1100, radiopaque marker beads are embedded in a tether cord at regular intervals, and arranged in pairs, such that a line connecting one pair of beads is at least partly orthogonal to a line connecting the other pair of beads. As the tether cord is stretched, the resulting deformation causes the marker beads to separate from one another. The amount of displacement is correlated to an axial tensile force. It is recognized that the amount of stretch in the tether may be small, so a vision system (e.g., smart-phone based camera app) may be helpful in detecting differences.

To improve accuracy, the position of the marker beads could be recorded prior to implantation and/or prior to any tensioning; this image could be used as a benchmark for subsequent analysis. Since the beads are radiopaque this evaluation could be done post-op with an x-ray or CT. Gross failure of the cord could also be detected if the beads are displaced from the centerline of the tether or have significant axial displacement.

Figure 13A:
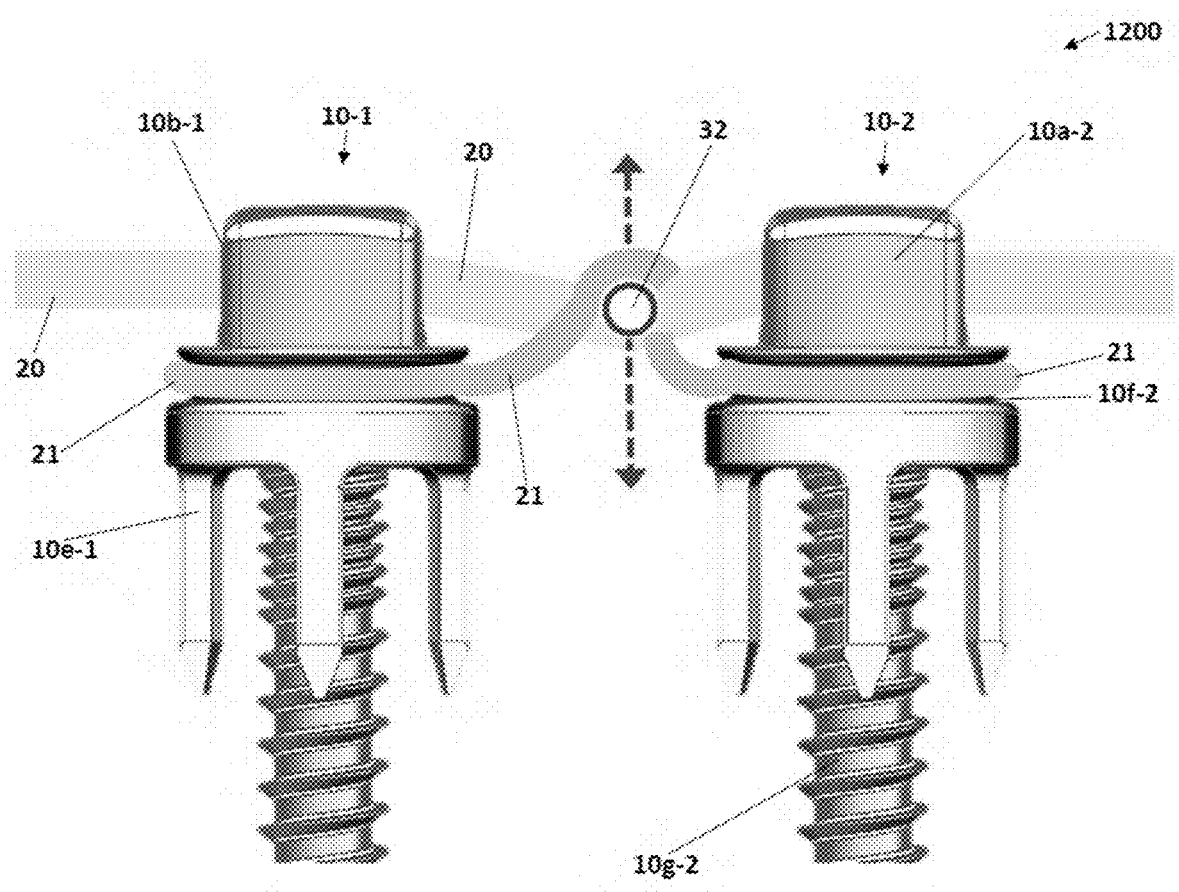
FIG. 13A is a side elevational schematic representation of a pair of bone anchoring assemblies used with an apparatus and methods according to another embodiment of the present invention.

FIG. 13A is a side elevational schematic representation of a pair of bone anchoring assemblies 10-1 and 10-2 used with an apparatus and methods 1200 according to another embodiment of the present invention. In some embodiments, each bone anchoring assembly 10 includes a first pathway 10b for a first flexible connector 20, and a second, spaced apart tether pathway 10f for a second tether pathway 10f. In the example show in FIG. 13A, the first pathway 10b extends through the heads 10a. The second tether path 10f extends in a circumferential groove of a corresponding anchor 10e. Although what are shown and described are vertically displaced tether pathways, yet other embodiments in the present invention pertain to multiple tether pathways that are spaced apart in any direction.

Preferably, the two flexible connectors 20 and 21 are interconnected between the bone anchors 10-1 and 10-2. As shown, the interconnection of FIG. 13A is a simple looping of one flexible connector around (either above or below) the other flexible connector. Preferably, one of the flexible connectors (tether 20 shown in FIG. 13A) includes a visual or radiopaque marker 32 which is the path that is configured to be placed at the interconnection between the tethers.

In some embodiments, the tension in the second flexible connector 21 is not adjustable, whereas tension is adjustable in the first flexible connector 20. As the degree of tension in tether 20 changes, the location of the marker 32 correspondingly changes. As one example, as shown in FIG. 13A, an increase in the tension of tether 20 will result in vertically upward movement of marker 32. In some embodiments, the two tethers 20 and 21 can be fabricated from different materials, fabricated in different methods, or otherwise different. In such embodiments, the second tether 21 is not relied upon for interconnection of the two vertebrae, and is instead adapted and configured to place a pre-determined range of loads on tether 20 by way of the looping interconnection. In yet other embodiments, each of the tethers can be in a state of tension, and in still further embodiments one tether can interconnect a first pair of bone anchors and the other tether can interconnect a second pair of bone anchors, in which either one or both members of the second pair of bone anchors are different than members of the first pair of bone anchors.

In this embodiment 1200 two tethers connect two bone anchors (attached via sets screws and loops around the staples, respectively), but they do so with a crossing arrangement as shown below. The tethers are also constructed so that they are of different stiffness. A visual marker is placed on one of the tethers, preferable in the location where the tethers cross.

Upon initial tensioning, the crossed arrangement, and thus the marker bead, will find an equilibrium point in the vertical plane based on the relative stiffness of the two tethers. As additional tension is applied more relative tension will be assumed by the stiffer tether because it cannot stretch as much as the more compliant tether. This would cause the marker to shift the vertical plane (up in the example).

The amount of vertical shift of the marker bead could be correlated to the relative tension between the two tethers. This would give the surgeon an indication of if tension is increase, decreasing, or staying stable. If the marker is radiopaque this assessment could be done via x-ray or CT.

Figure 13B:
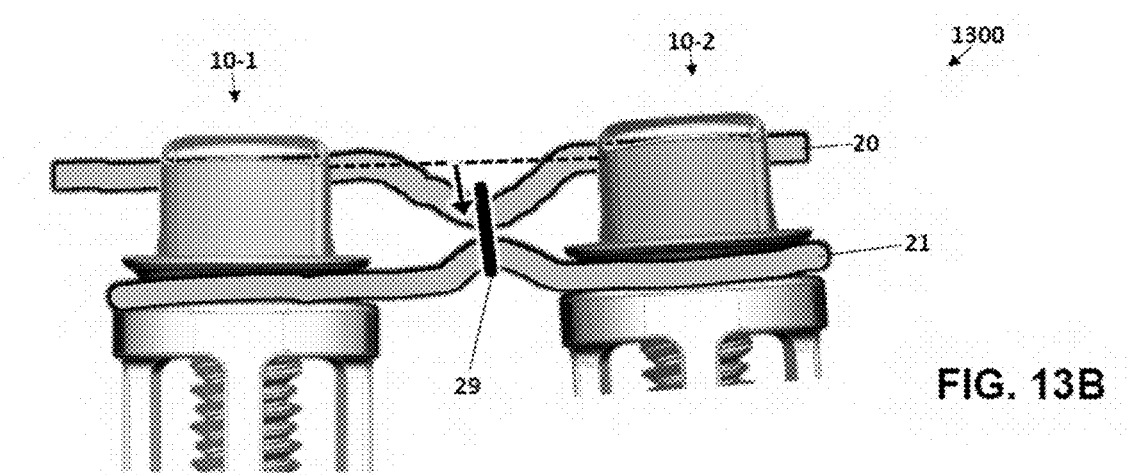
FIGS. 13B and 13C show side elevational schematic representations of an apparatus and method according to yet another embodiment of the present invention.
Figure 13C:
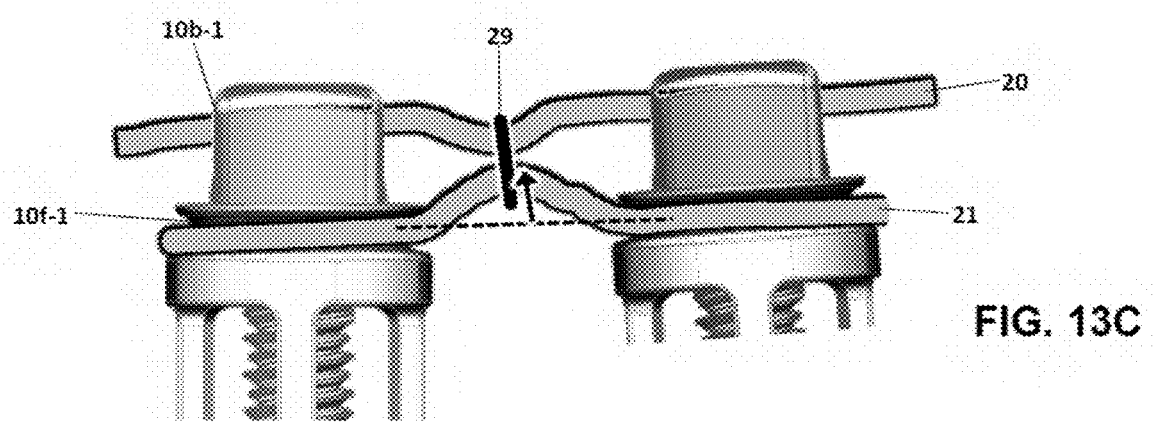

FIGS. 13B and 13C show side elevational schematic representations of an apparatus and method 1300 according to yet another embodiment of the present invention. Similar to embodiment 1200 discussed above, embodiment 1300 discloses a pair of interconnected tethers 20 and 21 located in two different pathways 10b and 10f, respectively. Instead of the looping interconnection shown in FIG. 13A, the tethers 20 and 21 of embodiment of 1300 are shown interconnected by a structure 29 such as a suture or clamp. In some embodiments, the suture is prepared and applied prior to installation of the tethers, and in yet other embodiments the suturing is accomplished after the anchors and tethers have been implanted. As another example, the present invention contemplates any type of clamp, including, as examples medical connectors related to electrical cable "zip" ties, or to crimped metal clamps.

Referring to FIG. 13B, in can be seen that the location of the interconnection of the tethers 20 and 21 is displaced downwardly a first amount (as indicated by the downward arrow) in correspondence to the amount of tension in tether 20. However, when tension is applied to tether 20 it tends to achieve a straighter configuration, and the upward deflection of the interconnection (as identified by the upward arrow) is greater than this upward deflection in FIG. 13B.

In a manner similar to that for embodiment 1200, a measurement or assessment of the change in the location of the interconnection can provide to the surgeon an indication of the degree of tension in tether 20. In yet other embodiments, the interconnection 29 comprises a suture having a predetermined fracturing strength, and the surgeon can assess the degree of tension in tether 20 by tensioning tether 20 until interconnection 29 fractures. After that fracture, the resultant tension in tether 20 will be less than the pre-fracture tension.

Sound and/or vibration can be used to estimate tension in a section of tether. A tensioned tether acts analogously to a tensioned guitar string: as more tension is added, the frequency of vibration changes and the pitch goes up. It is conceivable that a smartphone app could be used to analyze the frequency of a tether as the surgeon "plucks" it. Or a plurality of reference or "tuning" tethers could be mounted to a board, each of such tuning tethers under a different tension, so as to permit the surgeon to match the degree of tension in tether 20 to one of such tuning tethers. The correlation between frequency and tension could be generated via benchtop testing. This concept would work especially well for small diameter tethers and tethers made from metallic materials.

Sympathetic vibration could be used to assess the natural frequency of the implanted tether (like two identical tuning forks causing each other to vibrate). An instrument would contain a section of tether with an adjustable gauge length and a way to adjust and measure the tension. The surgeon would match the gauge length the implanted length of the tether. The surgeon would then iteratively adjust the tension, pluck the length of tether in the instrument, and see if a vibration is induced in the length of tether in the instrument. If there is vibration in the implanted tether, then it can be concluded that the tension matches. This method tension assessment is useful with small diameter, highly tensioned, and potentially metallic tethers.

Figure 14:
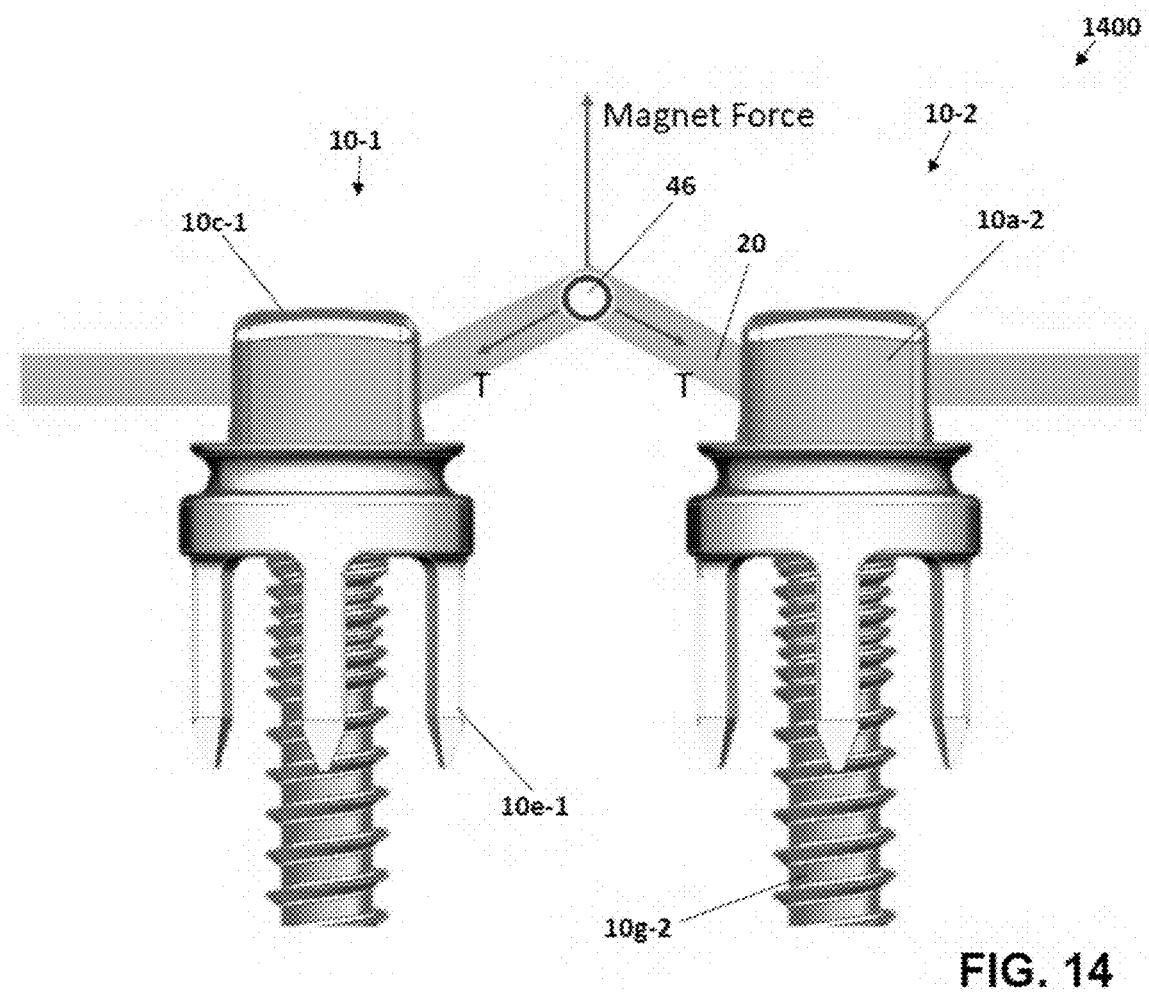
FIG. 14 is a side elevational schematic representation of a pair of bone anchors interconnected by a flexible member according to another embodiment of the present invention.

It is possible to take advantage of the magnetic force-displacement to estimate tension in a length of tether, as shown in FIG. 14. To accomplish this the tether includes metallic material (wire cable, e.g.) or a polymer tether must be embedded with a metallic, or possibly permanent magnetic, material. Embodiment 1400 shows an example of this, with a permanent magnet bead embedded in the tether although this could also take the form of a metallic wire or series of beads. The concept uses a force balance in which the tension along the axis of the tether is counteracted by a vertical (or lateral) force induced from a magnetic field. If the gauge length of the tether and the vertical/lateral displacement of the tether can be measured, it can be correlated to the axial tension in the tether.

Magnetic actuation and measurement could be accomplished in several ways, including:

1) A magnetic instrument could be introduced into the chest cavity (during the index procedure) to act on the magnetic material in the tether. The displacement could be measured using a ruler, for example. This method may be preferable because the displacement in the tether could be achieved without contacting the tether (and risking cutting/fraying/damaging it).

2) Once the tether is implanted magnetic actuation/displacement could be achieved with an external magnetic actuator (outside the skin). A CT or x-ray could be obtained with the external magnet acting on the internal tether. Vertical/lateral displacement could be measured on the x-ray/CT image and correlated to tension.

Figure 15A:
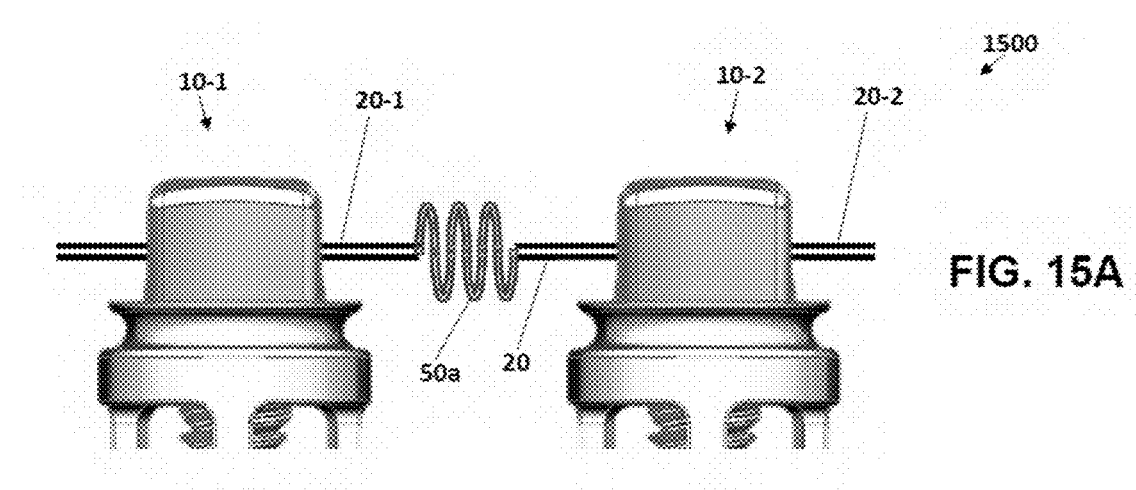
FIG. 15A is a side elevational schematic representation of a pair of bone anchors interconnected by a flexible member according to another embodiment of the present invention, prior to tensioning.
Figure 15B:
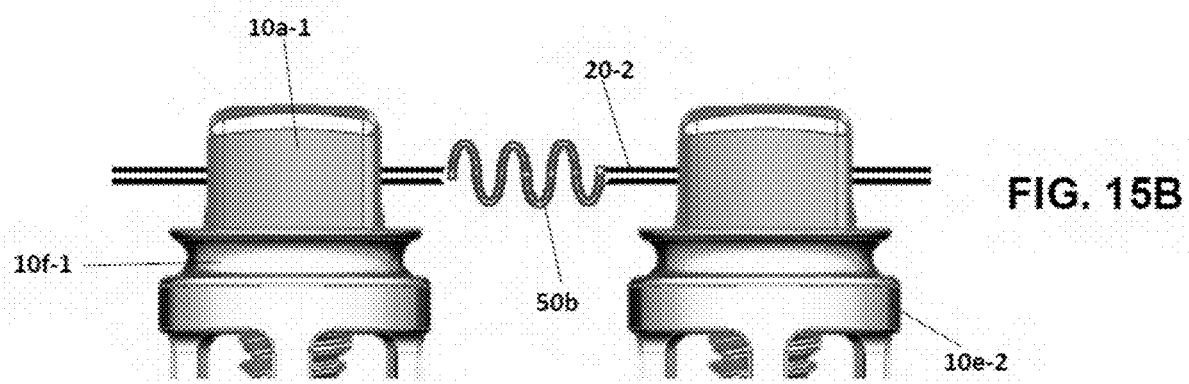
FIG. 15B is a view of the apparatus of FIG. 15A, after tensioning.

FIGS. 15A and 15B depict an apparatus and method 1500 according to another embodiment of the present invention. FIGS. 15A and 15B show a pair of adjacent bone anchors 10-1 and 10-2 each coupled to a different bone segment. Embodiment 1500 includes a flexible connector 20 that is a composite of two different flexible connectors. In one embodiment, a flexible connector 20 as previously discussed has placed within a spring 50. The elasticities of tether 20 and spring 50 are different. As one example, a tether 20 can be fabricated from a flexible organic material, and spring 50 can be a metallic spring (such as a coil spring). The ends of the tether segments 20 can be mechanically attached to corresponding ends of the spring 50. The spring constant for spring 50 is chosen such that tether tensions in the desired range are achieved with readily detectable changes in the spacing of the coils. Therefore, the visual or x-ray measurement methods previously discussed can determine the coil spacing.

Figure 16A:
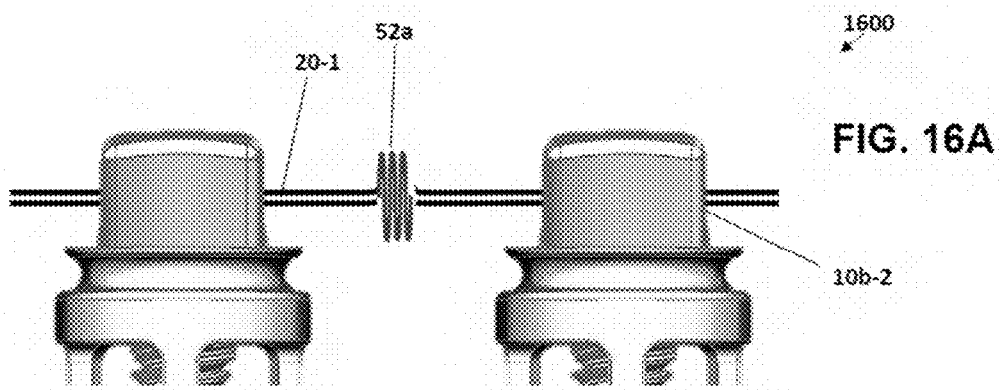
FIG. 16A is a side elevational schematic representation of a pair of bone anchors interconnected by a flexible member according to another embodiment of the present invention, prior to tensioning.
Figure 16B:
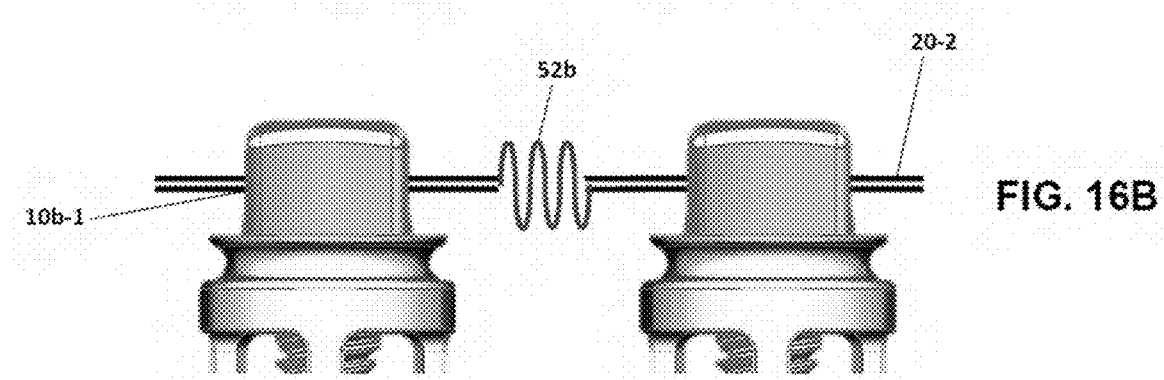
FIG. 16B is a view of the apparatus of FIG. 16A, after tensioning.

In still further embodiments 1600 shown in FIGS. 16A and 16B, the spring 52 is fabricated with a pre-determined spring constant, and further, a pre-determined preload. As such, when the tether assembly is initially assembled (e.g., FIG. 16A), the coils of spring 50a are generally collapsed, and in visually or radiographically detectable proximity. However, when a pre-determined tension is achieved, the coils of the spring extend apart and out of contact with each other as the pre-determined preload is exceeded. Therefore, an initial tension load can be assessed by detection of the spring coils coming out of mutual contact.

In still further embodiments, multiple springs 52 can be placed in series. Since the entire tension force goes through each spring, each spring can be fabricated to a different preload. At a first pre-determined tension load, the coils of the first spring would come out of contact with each other. As the amount of tension is increased, then the coils of the second spring come out of contact.

Figure 16C:
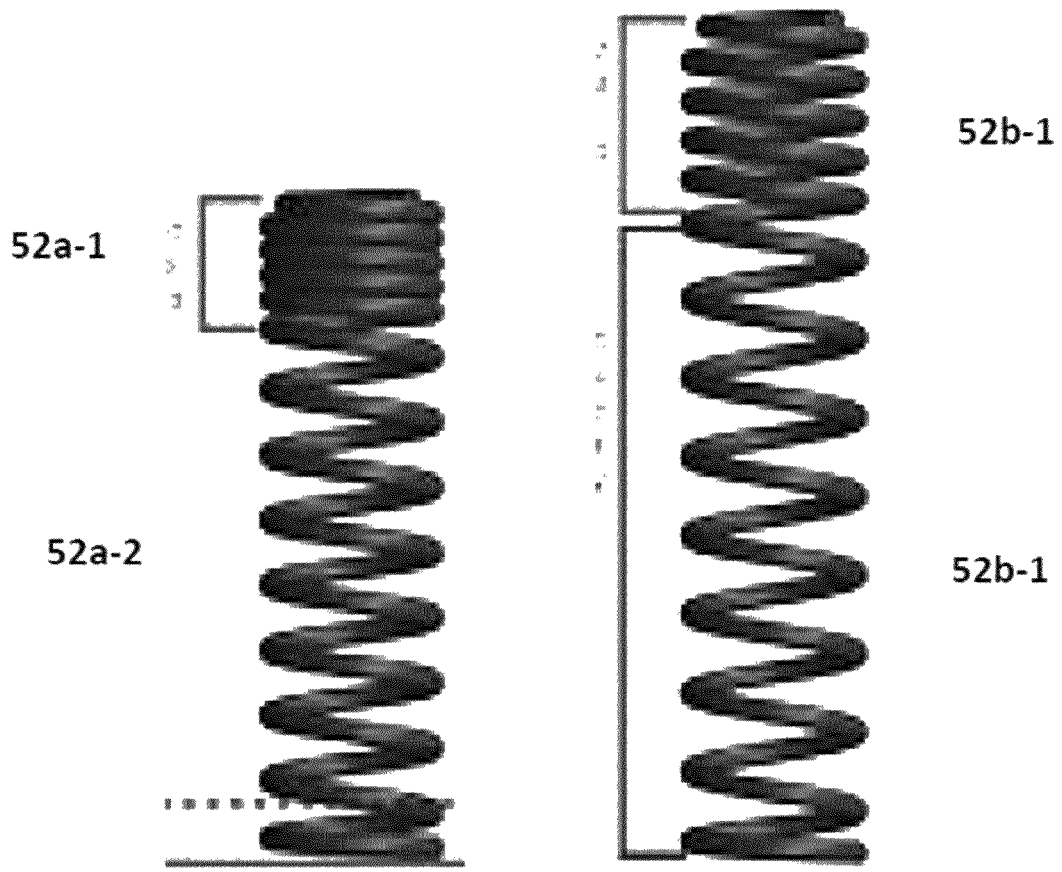
FIG. 16C is a schematic representation of springs usable in the apparatus of FIG. 16A.

FIG. 16C shows schematic representations of a preloadable spring 52 according to one embodiment of the present invention, and usable in the system. It is understood that the spring 52 can includes a first section 52a-1 having a preload that is in series with a second section 52a-2. Tension is placed on the ends of the spring 52, the second section 52b-2 extends first, until the load across the spring exceeds the preload of section 52b-1. Once that preload is attained, both of the -1 and -2 spring sections continue to extend, based on their individual spring constants.

It should be appreciated that various features of the present disclosure also provide for detecting and measuring a decrease in tension of the tether 20 that may occur over time due to a slippage between the tether 20 and the bone anchors 10.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

Statements Describing Some of the Various Embodiments Described Herein Include the Following:

A method for applying a tension force between a pair of bone anchors, comprising:
attaching a first bone anchor to a first vertebra;
attaching a second bone anchor to a second vertebra;
attaching a first portion of a flexible member to the first bone anchor;
attaching a second portion of the flexible member to the second bone anchor such that there is slack in the middle portion of the flexible member between the first and second portions;
reducing the length of the middle portion and removing the slack;
measuring the size of a feature of the middle portion after said removing;
tensioning the middle portion after said measuring;
remeasuring the size of the feature of the middle portion after said tensioning; and
comparing the measured size to the remeasured size and determining the state of tension in the middle portion.

A method for applying a tension force between a pair of vertebra, comprising:
attaching a flexible member between adjacent bone anchors, each anchor fixed to a different vertebra such that there no substantial tension in the middle portion of the flexible member between the adjacent bone anchors;
measuring the distance between a first pair of markers on the substantially untensioned flexible member;
measuring the distance between a second pair of markers on the substantially untensioned flexible member, at least one of the second pair being different than either of the first pair;
tensioning the middle portion after said measuring;
remeasuring the distance between the first pair of markers on the flexible member after said tensioning;
remeasuring the distance between the second pair of markers on the flexible member after said tensioning; and
comparing the measured distance to the remeasured distances and determining the state of tension in the middle portion.

A system for assessing the tension in an implantable flexible member interconnecting two bones, comprising:
an implantable body adapted and configured to provide substantially no resistance to compression of the body but able to support a tensile load within a predetermined range of loads from a first lower load to a second higher load and having a predetermined elasticity within the range, said body having a first width at the first lower load and a second small width at the first higher load;
a camera for detecting the image of the implanted said body; and
a processor for measuring the implanted width of said body, said processor including a database correlating the width of said body to a state of tension in said body.

An implantable flexible member for interconnecting two bones, comprising:

an implantable body having a length and width and comprising a material and adapted and configured to provide substantially no resistance to compression of the body but able to support a tensile load within a predetermined range of loads and having a predetermined elasticity within the range; and
a plurality of spaced apart symbols on the body in a predetermined pattern.

An implantable flexible member for interconnecting two bones, comprising:
an implantable body having a length and width and comprising a material and adapted and configured to provide substantially no resistance to compression of the body but able to support a tensile load within a predetermined range of loads and having a predetermined elasticity within the range; and
at least one symbol placed on the unloaded body in a predetermined shape, wherein loading the body in tension within the range of loads distorts the predetermined shape.

An implantable flexible member for interconnecting two bones, comprising:
an implantable body having a length and width and constructed to provide substantially no resistance to compression of the body but able to support a tensile load along the length within a predetermined range of loads and having a predetermined elasticity within the range; and
at least one frangible member placed with the body and adapted and configured to support a predetermined portion of the tensile load, said frangible member adapted and configured to break at a predetermined tensile force when the body is loaded within the predetermined range of loads.

A system for assessing the tension in an implantable flexible member interconnecting two bones, comprising:
an implantable body having a length and width and constructed of a plurality of strands of material and adapted and configured to provide substantially no resistance to compression of the body but able to support a tensile load within a predetermined range of loads from a first lower load to a second higher load and having a predetermined elasticity within the range, the weave having a first strand spacing at the first lower load and a second strand spacing at the second higher load;
a source of light adapted and configured to be placed on one side of said body; and
a detector of light placed on the opposite side of said body and providing a signal corresponding to the light transmitted through said body.

A system for assessing the tension in an implantable flexible member interconnecting two bones, comprising:
an implantable body having a length and width and constructed of a plurality of strands of material and adapted and configured to provide substantially no resistance to compression of the body but able to support a tensile load within a predetermined range of loads from a first lower load to a second higher load and having a predetermined elasticity within the range, the weave having a first strand spacing at the first lower load and a second strand spacing at the second higher load; and
a quantity of liquid dye placed on one side of said body;
wherein the quantity of dye and said body exhibit a first physical interaction at the first lower load and a second different physical interaction at the second higher load.

A system for assessing the tension in an implantable flexible member interconnecting two bones, comprising:
an implantable body having a length and width and constructed of a plurality of strands of material and adapted and configured to provide substantially no resistance to compression of the body but able to support a tensile load within a predetermined range of loads from a first lower load to a second higher load and having a predetermined elasticity within the range, the weave having a first strand spacing at the first lower load and a second strand spacing at the second higher load;

a quantity of a first liquid dye in contact with one side of said body; and a quantity of a second different dye in contact with the opposite side of said body;

wherein the first of dye and the second of dye exhibit a first interaction in the weave at the first lower load and a second different interaction in the weave at the second higher load.

A system for assessing the tension in an implantable flexible member interconnecting two bones, comprising:

a first bone anchor having a primary connector pathway and a secondary connector pathway, the primary pathway being spaced apart from the secondary pathway;

a second bone anchor have a primary connector pathway and a secondary connector pathway, the primary pathway being spaced apart from the secondary pathway;

a first flexible member extending between said first bone anchor and said second bone anchor along the primary pathway; and a second flexible member extending between said first bone anchor and said second bone anchor along the second pathway, said second flexible member looping around said first flexible member.

A system for assessing the tension in an implantable flexible member interconnecting two bones, comprising:

a first bone anchor having a primary connector pathway and a secondary connector pathway, the primary pathway being spaced apart from the secondary pathway;

a second bone anchor have a primary connector pathway and a secondary connector pathway, the primary pathway being spaced apart from the secondary pathway;

a first flexible member extending between said first bone anchor and said second bone anchor along the primary pathway; and a second flexible member extending between said first bone anchor and said second bone anchor along the second pathway, said second flexible member being interconnected to said first flexible member in between said first bone anchor and said second bone anchor.

An implantable flexible member for interconnecting two bones, comprising:

an implantable body having a length and width and constructed to provide substantially no resistance to compression of the body but able to support a tensile load along the length within a predetermined range of loads and having a predetermined elasticity within the range, said body including a folded region; and at least one frangible member placed around the fold and adapted and configured to support a predetermined tensile load, said frangible member adapted and configured to break and release the fold if the tensile force exceeds the predetermined tensile force.

A method for applying a tension force between a pair of vertebra, comprising:

attaching a flexible member between adjacent bone anchors, each anchor fixed to a different vertebra such that there no substantial tension in the middle portion of the flexible member between the adjacent bone anchors, the flexible member being responsive to a magnetic field;

tensioning the flexible member;

measuring the configuration of the tensioned flexible member;

applying an external magnetic field to the tensioned tether;

remeasuring the configuration of the tensioned flexible member during said applying; and comparing the measured configuration to the remeasured configuration and determining the state of tension in the middle portion.

An implantable flexible member for interconnecting two bones, comprising:

a first implantable body having a length and a first end and comprising a first material and adapted and configured to provide substantially no resistance to compression of the body but able to support a tensile load within a first predetermined range of loads and having a first predetermined elasticity within the first range;

a second implantable body having a length and a second end and comprising a second material and adapted and configured to provide substantially no resistance to compression of the body but able to support a tensile load within a second predetermined range of loads and having a second predetermined elasticity within the second range; and a spring having two ends, one spring end being attached to the first end and the other spring end being attached to the second end, said spring having a third predetermined elasticity within a third predetermined range of loads, the third elasticity being less than the first elasticity within the third range and also being less than the second elasticity within the third range.

A method for applying a tension force between a pair of vertebra, comprising:

attaching a spring having a preloaded portion with a collapsed initial configuration, the spring being attached at opposite ends between adjacent bone anchors, each anchor implanted to a different vertebra;

applying an increasing tension force between the implanted bone anchors that passes through the spring;

observing the configuration of the preloaded portion during said applying; and locking the tension force between the implanted anchors after the preloaded portion extends out of the collapsed configuration.

An implantable flexible member for interconnecting two bones, comprising:

a first implantable body having a length and a first end and comprising a first material and adapted and configured to provide substantially no resistance to compression of the body but able to support a tensile load within a first predetermined range of loads and having a first predetermined elasticity within the first range;

a second implantable body having a length and a second end and comprising a second material and adapted and configured to provide substantially no resistance to compression of the body but able to support a tensile load within a second predetermined range of loads and having a second predetermined elasticity within the second range; and a spring having two ends, one spring end being attached to the first end and the other spring end being attached to the second end, said spring having a portion with a predetermined preloaded;

wherein a tension load applied from said first body to said second body passes through the preloaded portion, and the predetermined preload is selected to correspond to the desired tension interconnecting the two bones.

Still Further Embodiments are Described by Combining any of Previous Paragraphs [0120] Through [0135] with One or More of the Following Statements:

wherein the plurality of spaced apart symbols are printed on the body in a predetermined pattern.

wherein the plurality of spaced apart symbols are woven into the body in a predetermined pattern.

wherein the plurality of spaced apart symbols are braided into the body in a predetermined pattern.

wherein the plurality of spaced apart symbols are sutured onto the body in a predetermined pattern after implantation of the body.

wherein said spring is a coil spring, said coil spring including a first section of coils that are in preloaded contact prior to attachment to an implantable body.

wherein said spring is a coil spring having two portions in series, with a first portion of coils having a first spring constant and the second portion having a second, different spring constant.

which further comprises a marker located at the looping or interconnection of said first flexible member and said second flexible member.

wherein the marker is adapted and configured to be visually distinctive, and which further comprises a camera adapted and configured to provide a signal to a processor corresponding to the image of the implanted marker.

wherein the marker is radiopaque.

which further comprises a clamp for interconnecting said first flexible member and said second flexible member.

which further comprises a suture for interconnecting said first flexible member and said second flexible member.

wherein said implantable body comprises a plurality of strands arranged in one of a weave, braid, or knitting.

wherein the distance between the first pair of markers is not parallel to the distance between the second pair of markers.

wherein the distance between the first pair of markers is substantially orthogonal to the distance between the second pair of markers.

wherein said comparing includes calculating the ratio of the [change in distance of the first pair of markers] to the [change in distance of the second pair of markers].

which further measuring the distance between a pair of closely spaced markers before said tensioning and comparing the measure distance to the known distance between the closely spaced markers prior to said attaching.

which further measuring the distance between a pair of closely spaced markers after said tensioning and comparing the measure distance to the known distance between the closely spaced markers prior to said attaching.

wherein the feature is the width of the middle portion.

wherein the feature is the diameter of the middle portion.

wherein the feature is a symbol printed on the middle portion.

wherein the flexible member is woven and feature is a pattern in the weave.

wherein the flexible member is woven and feature is a gap in the weave.

wherein said measuring and said remeasuring are performed optically.

which further comprise a source of light adapted and configured to illuminate said implanted body.

wherein the symbols are spaced apart along the length of the body.

wherein the symbols are spaced apart across the width of the body.

wherein some of the symbols are spaced apart across the width of the body and other of the symbols are spaced apart across the width of the body.

wherein the symbols are radiopaque.

wherein the symbols have linear edges.

wherein the symbols have visually distinct edges.

wherein the symbols are lines.

wherein the symbols are closely spaced pairs of parallel lines.

wherein each the symbol has an area and an identifier of the center of the area.

wherein the area and the identifier are visually distinct.

wherein said body is a first body having a first length and a first width, and wherein the symbol comprises a second implantable body comprising a material adapted and configured to provide substantially no resistance to compression of the body.

wherein the second body has a second length including a middle portion and two opposing ends, each opposing end of the second body being attached to corresponding spaced apart locations along the first length of the body, the length of the middle portion of the second body being greater than the distance between the spaced apart locations.

wherein the middle portion of the second body forms at least a portion of the predetermined shape.

wherein the second body has a second length including a middle portion and two opposing ends, each opposing end of the second body being attached to corresponding spaced apart locations along the first length of the body, the middle portion of the second body being loosely guided on the first body between the spaced apart locations.

wherein the middle portion includes slack, and the slack forms at least a portion of the predetermined shape.

wherein the body is a weave of strands of a first material, and the frangible member is at least one strand of a second material within the body.

wherein the first material and the second material are the same.

wherein the first material and the second material are different.

wherein the length is a first length and the frangible member has a second length including a middle portion and two opposing ends, each opposing end of the frangible member being in load bearing attachment to corresponding locations along the first length of the body, the middle portion of the frangible member not being in load bearing attachment to said body.

wherein the frangible member breaks at a first predetermined tensile force, and which further comprises a second frangible member placed with the body and adapted and configured to support a predetermined portion of the tensile load, said frangible member adapted and configured to break at a tensile force when the body is loaded within the predetermined range of loads, the second tensile force being different than the first tensile force.

wherein the frangible member has a color that is different than the color of said body.

wherein the frangible member is visually distinct on said body.

which further comprises a processor for measuring the transmitted light, said processor including a database correlating the light transmitted through said body to a state of tension in said body.

which further comprises a smart phone, said smart phone receiving the signal.

wherein the physical interaction is the shape of the quantity of dye as a result of wicking into the implantable body.

wherein the first characteristic is the beading of the quantity on the surface of said implantable body and the second characteristic is penetration of a least a portion of the quantity into the implantable body.

wherein the first characteristic is the penetration of a least a portion of the quantity through the surface of said implantable body and the second characteristic is beading of the quantity on the surface of the implantable body.

wherein the mixing is a result of at least one of the first dye or the second dye wicking through the implantable body and into the other of the first dye or the second dye.

wherein the first characteristic is the beading of the quantity on the surface of said implantable body and the second characteristic is penetration of a least a portion of the quantity into the implantable body.

wherein the first characteristic is the penetration of a least a portion of the quantity through the surface of said implantable body and the second characteristic is beading of the quantity on the surface of the implantable body.

wherein the first liquid dye has a first higher viscosity and the second dye has a second lower viscosity.

wherein the first liquid dye has a first higher surface tension and the second dye has a second lower surface tension.

wherein the first liquid dye has a first color and the second dye has a second different color.

wherein the first interaction and the second interaction are mixings of the first dye and the second dye.

wherein the first dye and the second dye are immiscible, and the first interaction and the second interaction are penetrations of the first dye and the second dye into the weave.

wherein after implantation each primary pathway is displaced further from the bone surface than each secondary pathway.

wherein said first bone anchor includes means for adjusting the length of said first flexible member between said first bone anchor and said second bone anchor.

wherein decreasing the length of said first flexible member between said first bone anchor and said second bone anchor changes the shape of the portion of said second flexible member between said first bone anchor and said second bone anchor.

which further comprises a plurality of frangible members each placed around the fold and spaced apart from one another along the length of the fold.

wherein the flexible member includes at least one magnet.

wherein the flexible member includes at least one component that is magnetic.

wherein said spring has a preload and said spring is substantially not elastic below the preload.

wherein the first material and the second material are organic materials, and the spring is metallic.

wherein the second elasticity is equal to the first elasticity.

What is claimed is:

1. A system for interconnecting bones, the system comprising:
   an implantable member configured to be mechanically coupled to a first bone, configured to be mechanically coupled to a second bone, configured to provide substantially no resistance to compression of the implantable member, configured to support a tensile load within a predetermined range of tensile loads extending from a first load to a second load, configured to have a predetermined elasticity within the range of tensile loads, configured to have a first width at the first load, the first width being generally transverse to the first load at the first load, and configured to have a second width at the second load, the second width being generally transverse to the second load at the second load;
   a means for measuring the first width and the second width; and
   a means for calculating a tension between the first bone and the second bone based on the first width and the second width.

2. The system of claim 1, wherein the implantable member comprises a tether band.

3. The system of claim 2, wherein the means for calculating comprises a smart phone.

4. The system of claim 3, wherein the means for measuring comprises an optical detector.

5. The system of claim 1, wherein the means for calculating comprises a means for calculating the tension between the first bone and the second bone based on a Poisson Effect.

6. A system for interconnecting bones, the system comprising:
   a first bone anchor;
   a second bone anchor;
   an elastically deformable coupling connecting the first bone anchor to the second bone anchor, having a length extending between the first bone anchor and the second bone anchor, and having a width being generally transverse to the length;
   an optical device configured to observe the width and to generate data based thereon; and
   a computing device configured to calculate a tension between the first bone anchor and the second bone anchor based on the data.

7. The system of claim 6, wherein the optical device is configured to observe at least two dimensions of the coupling and to generate the data based thereon.

8. The system of claim 7, wherein the computing device is configured to calculate the tension between the first bone anchor and the second bone anchor based on a Poisson Effect.

9. The system of claim 7, wherein the coupling comprises a tether band.

10. The system of claim 9, wherein the computing device is configured to calculate the tension between the first bone anchor and the second bone anchor based on a Poisson Effect.

11. The system of claim 9, wherein the computing device comprises a smart phone.

12. The system of claim 11, wherein the computing device is configured to calculate the tension between the first bone anchor and the second bone anchor based on a Poisson Effect.

13. The system of claim 6, wherein the computing device comprises a smart phone.

* * * * *